United States Patent
Liang et al.

(10) Patent No.: US 11,690,912 B2
(45) Date of Patent: Jul. 4, 2023

(54) METHODS FOR TREATMENT OF RHEUMATOID ARTHRITIS AND ACCELERATED ATHEROSCLEROSIS WITH AN ANTI-APO B100 ANTIBODY

(71) Applicant: Abcentra, LLC, Los Angeles, CA (US)

(72) Inventors: Bertrand C. Liang, San Diego, CA (US); Stacey Ruiz, Beverly Hills, CA (US); Christopher John Farina, Los Angeles, CA (US)

(73) Assignee: Abcentra, LLC, Los Angeles, CA (US)

( * ) Notice: Subject to any disclaimer, the term of this patent is extended or adjusted under 35 U.S.C. 154(b) by 0 days.

(21) Appl. No.: 17/058,508

(22) PCT Filed: May 29, 2019

(86) PCT No.: PCT/US2019/034439
§ 371 (c)(1),
(2) Date: Nov. 24, 2020

(87) PCT Pub. No.: WO2019/232081
PCT Pub. Date: Dec. 5, 2019

(65) Prior Publication Data
US 2021/0214426 A1    Jul. 15, 2021

Related U.S. Application Data

(60) Provisional application No. 62/677,595, filed on May 29, 2018.

(51) Int. Cl.
| | | |
|---|---|---|
| *A61K 39/395* | (2006.01) | |
| *A61P 29/00* | (2006.01) | |
| *A61P 9/00* | (2006.01) | |
| *G01N 33/50* | (2006.01) | |
| *C07K 16/18* | (2006.01) | |
| *A61P 9/10* | (2006.01) | |
| *C07K 14/775* | (2006.01) | |
| *A61K 45/06* | (2006.01) | |
| *A61K 39/00* | (2006.01) | |
| *G01N 33/53* | (2006.01) | |

(52) U.S. Cl.
CPC ............ *A61K 39/3955* (2013.01); *A61P 9/10* (2018.01); *A61P 29/00* (2018.01); *C07K 16/18* (2013.01); *G01N 33/50* (2013.01); *A61K 45/06* (2013.01); *A61K 2039/505* (2013.01); *C07K 14/775* (2013.01); *C07K 2317/21* (2013.01); *C07K 2317/34* (2013.01); *C07K 2317/56* (2013.01); *C07K 2317/565* (2013.01); *C07K 2317/90* (2013.01); *G01N 33/53* (2013.01)

(58) Field of Classification Search
CPC .. A61K 39/3955; C07K 16/18; C07K 14/775; A61P 9/10; A61P 29/00
See application file for complete search history.

(56) References Cited

U.S. PATENT DOCUMENTS

| | | | |
|---|---|---|---|
| 8,318,161 B2 * | 11/2012 | Esue | A61P 9/10 |
| | | | 424/139.1 |
| 2007/0003548 A1 | 1/2007 | Heavner et al. | |
| 2009/0208503 A1 * | 8/2009 | Carlsson | A61P 43/00 |
| | | | 435/7.1 |
| 2010/0286025 A1 | 11/2010 | Anantharamaiah et al. | |
| 2015/0064195 A1 | 3/2015 | Kupper et al. | |
| 2017/0342493 A1 | 11/2017 | Barril et al. | |

FOREIGN PATENT DOCUMENTS

| | | |
|---|---|---|
| WO | WO-02/080954 A1 | 10/2002 |
| WO | WO-2008/104194 A1 | 9/2008 |

OTHER PUBLICATIONS

International Preliminary Report on Patentability for International Patent Application No. PCT/US2019/034439, dated Dec. 1, 2020 (12 pages).

Szekanecz et al., "Accelerated atherosclerosis in rheumatoid arthritis," Ann N Y Acad Sci. 1108:349-58 (2007).

\* cited by examiner

*Primary Examiner* — Zachary C Howard
(74) *Attorney, Agent, or Firm* — Clark & Elbing LLP

(57) ABSTRACT

Compositions and methods for treating rheumatoid arthritis and/or accelerated atherosclerosis are provided, including an inhibitor of oxidized or malondialdehyde-modified low density lipoprotein (LDL) for administration to a subject. Exemplary inhibitors of oxidized LDL include an anti-oxidized LDL antibody, which results in a reduction in the secretion of pro-inflammatory cytokine from primary monocyte in vitro and the plasma cytokine level of inflammatory cytokine in vivo.

18 Claims, 5 Drawing Sheets
Specification includes a Sequence Listing.

METHODS FOR TREATMENT OF RHEUMATOID ARTHRITIS AND ACCELERATED ATHEROSCLEROSIS WITH AN ANTI-APO B100 ANTIBODY

CROSS-REFERENCE TO RELATED APPLICATIONS

This application includes a claim of priority under 35 U.S.C. § 119(e) to U.S. provisional patent application No. 62/677,595, filed May 29, 2018, the entirety of which is hereby incorporated by reference.

FIELD OF INVENTION

This invention relates to treatment of rheumatoid arthritis and atherosclerosis.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Rheumatoid arthritis (RA) is a chronic inflammatory disease that symptomatically affects the lining of the joints (synovium), causing damage to both the joints and bone. Inflammation resulting from activated macrophages and lymphocytes produces reactive oxygen species (ROS), which modifies low-density lipoprotein (LDL) cholesterol that enters the subendothelial space. The oxidized LDL (oxLDL) is then taken up my macrophages, which are converted into foam cells, inducing the fatty streaks that precede plaque development. Foam cells are pro-inflammatory and release cytokines that serve as chemoattractants for both monocytes and T cells, which are known to play a significant role in atherosclerosis development. These molecules also effect the proliferation and migration of vascular smooth muscle cells (VSMCs), likely through binding to lectin-type oxidized LDL receptor 1 (LOX-1), which plays an important role in atherosclerotic plaque progression. This inflammation within the plaque leads to continued plaque growth and plaque instability.

RA patients have increased levels of total cholesterol, LDL, and triglycerides compared to normal subjects. Therefore, the chronic inflammatory status of RA patients and high lipid levels, which can be oxidized and further incite inflammation, put RA patients at an increased risk of developing a cardiovascular disease (CVD), and the higher rate of premature mortality associated with RA is attributed, at least in part, to CVD. Moreover, RA accounts for approximately 30% of the risk for developing CVD.

Several pro-inflammatory cytokines found in circulation including TNFα, IL-1β, IL-6, MCP-1, and CRP are the targets of disease-modifying anti-rheumatic drugs (DMARDs). Immunotherapy intervention with DMARDs for one year resulted in decreased markers of inflammation and reduced autoantibody titers to oxLDL in patients with early stage RA (previously untreated RA). In another study in patients without a diagnosis of coronary heart disease who had RA for a mean of 12.8±10.3 years, circulating levels of oxLDL were significantly increased compared to control subjects, even though the amounts of native LDL between the groups were similar. Subset analysis of RA patients with carotid plaques showed that they had significantly higher levels of oxLDL than in RA patients without carotid plaques. Interestingly, the amount of anti-oxLDL antibodies negatively correlated with carotid intima-media thickness (IMT). However, in those patients receiving glucocorticoids, anti-oxLDL antibodies negatively correlated with prednisone dose, which is a common DMARD, indicating that atheroprotection occurred when these antibodies are reduced. It remains an unmet medical need to identify effective therapeutics and treatment methods for patients with RA.

Therefore it is an objective of the present invention to provide compositions for use in and methods for treating, reduce the severity or likelihood of rheumatoid arthritis, accelerated atherosclerosis, or both in a subject.

SUMMARY OF THE INVENTION

The following embodiments and aspects thereof are described and illustrated in conjunction with compositions and methods which are meant to be exemplary and illustrative, not limiting in scope.

Methods for treating, reducing the severity of, slowing progression of or inhibiting rheumatoid arthritis, accelerated atherosclerosis, or both in a subject in need thereof are provided, which include administering to the subject an effective amount of an antibody or antibody fragment capable of binding to a fragment of apolipoprotein B100 (ApoB100), wherein the fragment of ApoB100 comprises an amino acid sequence of SEQ ID No.: 1 or an active site thereof, and wherein the antibody comprises one, two or three heavy chain complementarity determining regions (HCDRs) selected from the group consisting of HCDR 1 (HCDR1), HCDR 2 (HCDR2) and HCDR 3 (HCDR3) sequences of SEQ ID Nos: 2, 3 and 4, respectively, and one, two or three light chain complementarity determining regions (LCDRs) selected from the group consisting of LCDR 1 (LCDR1), LCDR 2 (LCDR2) and LCDR 3 (LCDR3) sequences of SEQ ID Nos: 5, 6 and 7, respectively. One aspect of the methods is for treating, reducing the severity of, slowing progression of or inhibiting rheumatoid arthritis in a subject. Another aspect of the methods is for treating, reducing the severity of, slowing progression of or inhibiting accelerated atherosclerosis in a subject with rheumatoid arthritis. Yet another aspect of the methods is for treating, reducing the severity of, slowing progression of or inhibiting both rheumatoid arthritis and accelerated atherosclerosis in a subject.

Also provided are methods of reducing the severity of or the likelihood of developing inflammation in a subject, which includes administering to the subject an effective amount of an antibody or antibody fragment capable of binding to a fragment of apolipoprotein B100 (ApoB100), wherein the fragment of ApoB100 comprises an amino acid sequence of SEQ ID No.: 1 or an active site thereof, and wherein the antibody comprises one, two or three heavy chain complementarity determining regions (HCDRs) selected from the group consisting of HCDR 1 (HCDR1), HCDR 2 (HCDR2) and HCDR 3 (HCDR3) sequences of SEQ ID Nos: 2, 3 and 4, respectively, and one, two or three light chain complementarity determining regions (LCDRs) selected from the group consisting of LCDR 1 (LCDR1), LCDR 2 (LCDR2) and LCDR 3 (LCDR3) sequences of SEQ ID Nos: 5, 6 and 7, respectively.

Further embodiments provide that the methods of treating, reducing the severity or likelihood of rheumatoid arthritis and/or accelerated atherosclerosis, or the methods of reducing the severity of or the likelihood of developing inflammation, include administering an inhibitor that inhibits, binds, blocks or occupies LDL, oxidized LDL (oxLDL) or malondialdehyde-modified epitope in LDL are provided. In one embodiment, the inhibitor is an anti-oxLDL antibody or an antigen-binding fragment thereof. In another embodiment, the inhibitor of oxidized LDL is a small molecule, a polypeptide, a peptide, or a nucleic acid molecule. In exemplary embodiments, the inhibitor of oxidized LDL is a monoclonal antibody targeting LDL, oxidized forms of LDL, or malondialdehyde (MDA)-modified epitope of LDL, the monoclonal antibody being such as orticumab (also known as BI-204; MLDL 1278A; RG 7418, anti-oxLDL).

In some embodiments, one or more of the methods disclosed herein further include administering one or more therapeutic agents, which optionally may be in combination with the antibody or antibody fragment disclosed herein. In some aspects, this additional therapeutic agent is a disease-modifying anti-rheumatic drug (DMARD) such as azathioprine, cyclophosphamide, cyclosporine, hydroxychloroquine sulfate, leflunomide, methotrexate, mycophenolate mofetil, and sulfasalazine. In other aspects, the additional therapeutic agent to an inhibitor of oxLDL is bis-phenyl (2-halophenyl)-1-imidazolylmethane, clotrimazole, tinidazole, nitroimidazole, 4-aminoquinolines, hydroxychloroquine, amodiaquine, copper sulphate, dehydrocholine, clotrimazole, suramin, pentamidine, dehydroemetine, metronidazole, nimorazole, phanquone, diloxanide, an anti-tumor necrotic factor (TNF) antibody, an anti-TNF peptide, and a nucleic acid encoding an anti-TNF antibody or peptide.

In some embodiments, one or more of the methods for treating, reducing the severity of, slowing progression of or inhibiting rheumatoid arthritis or a combination of rheumatoid arthritis and atherosclerosis (e.g., accelerated atherosclerosis), or for reducing inflammation, in a subject in need thereof is characterized by reduced amounts of inflammation markers such as monocyte chemoattractant protein-1 (MCP-1), tumor necrosis factor-alpha (TNFα) and interleukin 1 beta (IL-1β) in the plasma of the subject following administration of the antibody or antibody fragment, compared to those levels of the subject before administration. Further aspects of these embodiments include selecting a subject with an increased amount of one or more of the inflammation markers for the administration, and the increased amount is compared to a control subject free of symptoms of rheumatoid arthritis, atherosclerosis, or both.

Various embodiments of one or more of the disclosed methods include administering an initial dose of the antibody or antibody fragment in an amount of at least 5 mg/kg, or preferably at least 8 mg/kg. In some embodiments, an initial dose is sufficient to result in improvement and treatment of rheumatoid arthritis in a patient. In further embodiments, the methods include administering a plurality of subsequent doses of the antibody or antibody fragment in an amount that is at least about 2 mg/kg/week, at least about 2.5 mg/kg/two weeks, or at least about 6 mg/kg/month. Typically, an effective amount of the antibody or antibody fragment in the described method results in an antibody amount of at least 4 µg/mL in circulation, preferably at least 12 µg/mL in circulation. Further aspects provide that the methods result in an effective amount of the antibody or antibody fragment in an amount of at least 4 µg/mL in circulation, preferably at least 12 µg/mL in circulation for an extended period of time (e.g., at least 30 minutes, 1 hour, 2 hours, 3 hours, 4 hours, 1 day, 2 days, 3 days, 1 week, 2 weeks, 3 weeks, 1 month, 2 months or 3 months).

Other embodiments provide that one or more of the methods described herein include administering at least an initial dose of the antibody of approximately 800-900 mg, 900-1000 mg, 1000-1100 mg, 1100-1200 mg, 1200-1300 mg, 1300-1400 mg, 1400-1500 mg, or 1500-1600 mg. In some aspects, the methods include administering an initial dose of orticumab of approximately 1000-1500 mg, followed by subsequent doses of the antibody at 700-900 mg administered weekly for 2, 3, 4 or 5 weeks and/or even administered monthly for 1, 2 or 3 months.

Other exemplary embodiments of one or more of the methods disclosed herein include administering step-wise escalating doses of the antibody or antibody fragment. In this embodiment, an exemplary (starting) dose of a single-dose administration of the antibody (e.g., orticumab) is between 0.005 and 0.01 mg/kg (e.g., intravenously); and other exemplary dosage levels to be administered in the single-dose administration are between 0.01 and 0.15, between 0.15 and 0.75, between 0.75 and 2.5, between 2.5 and 7.5, and between 7.5 and 30 mg/kg (e.g., intravenously). For example, a starting dose of orticumab in a single-dose intravenous administration is 0.007 mg/kg; and other exemplary dosages can be 0.05, 0.25, 1.25, 5.0 or 15.0 mg/kg in subsequent single-dose intravenous administration. In another embodiment, a single-dose subcutaneous administration of the antibody (e.g., orticumab) is between 0.5 and 6 mg/kg, and a multiple-dose subcutaneous administration is also between 0.5 and 6 mg/kg. For example, an antibody against native or oxidized LDL at 1.25 mg/kg is administered subcutaneously. In various embodiments, the dosage is administered within a specified hour range of the day in each administration, and each dose in a multiple-dose treatment (e.g., 4 doses, 3 doses, 5 doses, or 6 doses) is administered at weekly intervals with a time window of ±1 day. In another example, the antibody (such as orticumab) disclosed herein is administered at between 300 mg and 450 mg (e.g., 360 mg) to a human subject, optionally followed by another dose between 300 mg and 450 mg (e.g., 360 mg) to the human subject where the second dose is at least 70 days (up to 91 days) apart from the first dose. The antibody (such as orticumab) may be formulated at a concentration of 100-170 mg/mL (e.g., 150 mg/mL) and for use in subcutaneous administration without further dilution, or diluted to a large volume for intravenous infusion.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 1A shows the amount of MCP-1(%) over different concentrations of anti-oxLDL antibody. ***p<0.001. FIG. 1B shows the amount of MCP-1(%) in the medium culturing monocytes that were unstimulated (NA) or stimulated with IL-1β (IL1β) in the presence of a control antibody or an anti-oxLDL antibody. MCP-1 levels from cell culture supernatant were measured;

MCP-1 levels from LPS-stimulated cells without antibody treatment was set to 100%; *p<0.05.

Figure 2A:
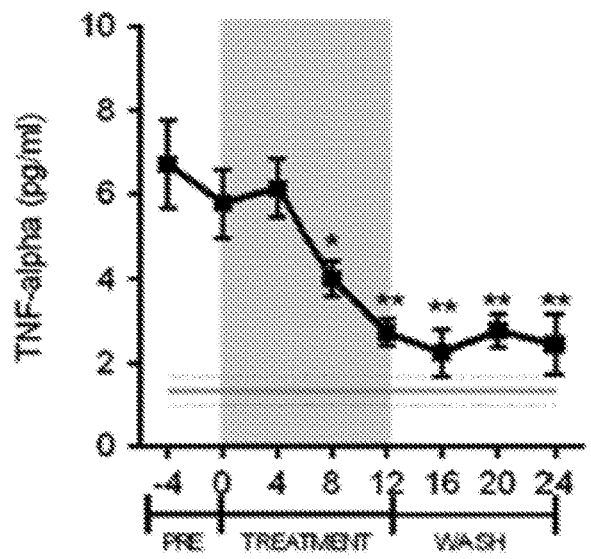
Figure 2B:
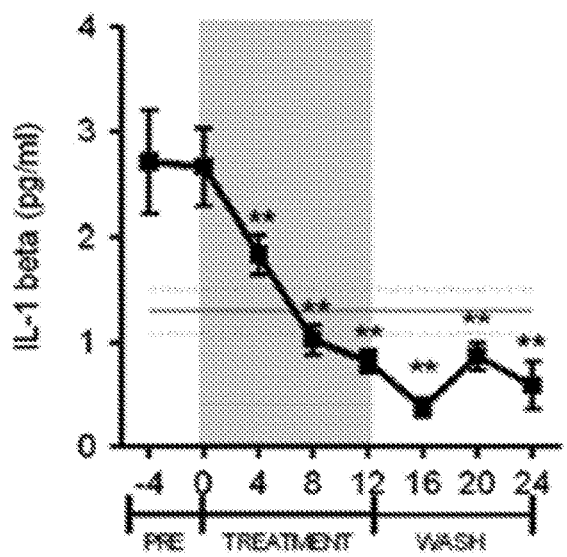

FIGS. 2A and 2B depict that the anti-oxLDL monoclonal antibody inhibits inflammation in vivo as characterized by the amounts of TNFα (FIG. 2A) and IL-1β (FIG. 2B). Changes in plasma inflammatory cytokines in response to diet and to the anti-oxLDL antibody treatment (weekly intravenous administration at 10 mg/kg over 12 weeks for a total of 13 doses) in rhesus macaques (n=6) were measured. The straight horizontal line between 1 and 2 of the y-axis in each of FIGS. 2A and 2B indicates the average plasma cytokine level in normal diet-fed control animals (n=20).

Figure 3:
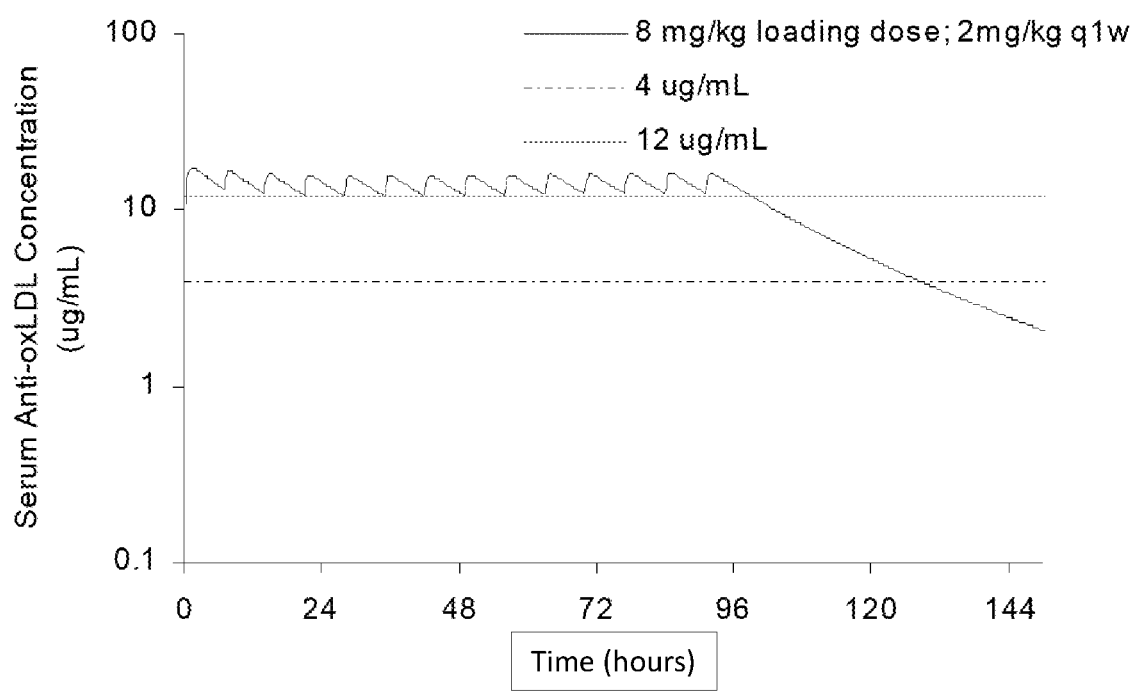

FIG. 3 depicts a simulated human pharmacokinetics (PK) profile after a subcutaneous (SC) loading dose of 8 mg/kg followed by a weekly SC dosing of 2 mg/kg. Dashed lines indicate two desired thresholds (4 μg/mL, generally lowest line, and 12 μg/mL, the higher dashed line) of the serum concentration of orticumab.

Figure 4A:
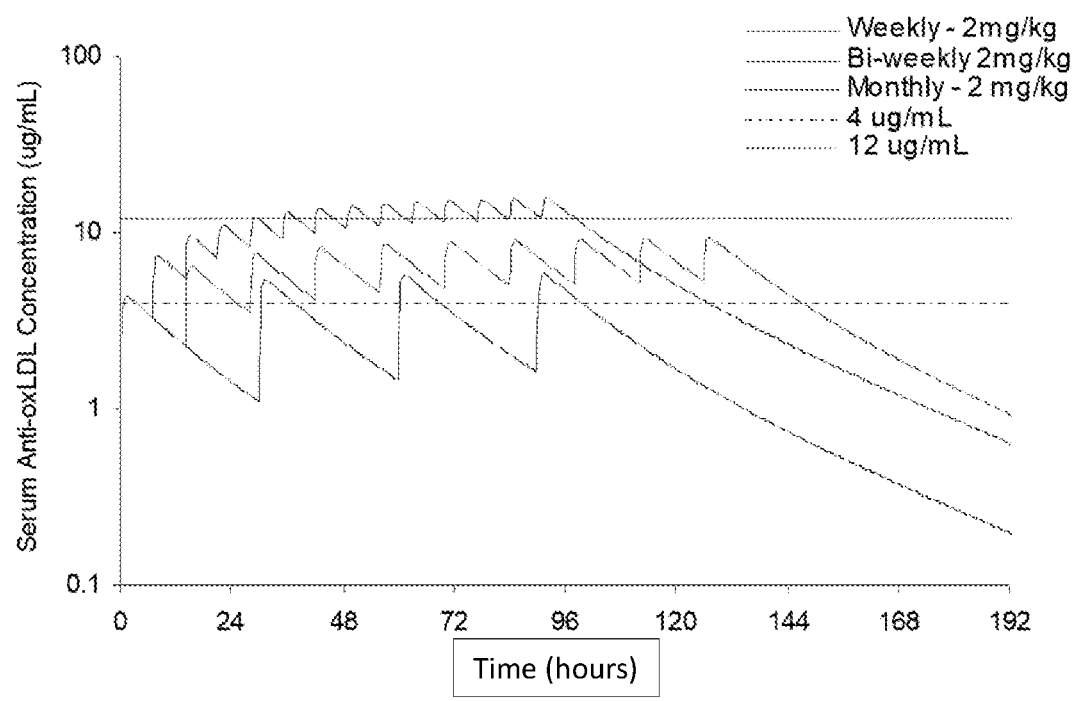
Figure 4B:
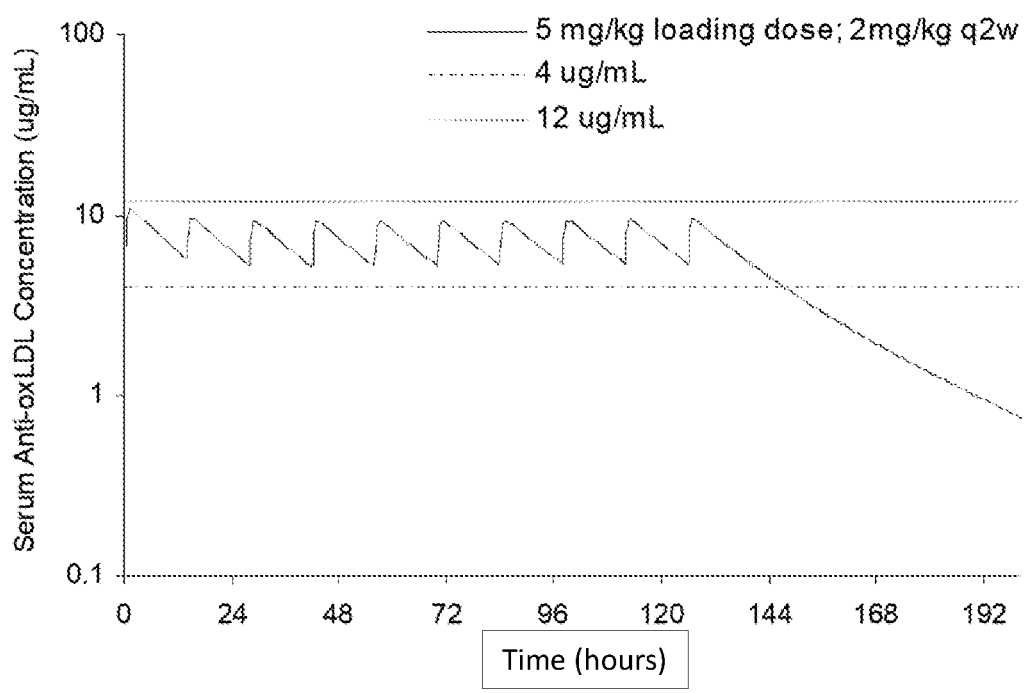

FIGS. 4A and 4B depict simulated human PK profiles based on SC dosing. In FIG. 4A, the highest solid line between 0 and 96 hours indicates dosing at a weekly frequency at 2 mg/kg; generally the middle solid line between 24 and 96 hours indicates dosing at a bi-weekly frequency at 2 mg/kg; and generally the lowest solid line indicates dosing at a monthly frequency at 2 mg/kg. In FIG. 4B, the solid line indicates a loading dose at 5 mg/kg and subsequent doses at 2 mg/kg every two weeks. Generally lower dashed line indicates a desired threshold of 4 μg/mL of the serum concentration of orticumab. Generally higher dashed line indicates a desired threshold of 12 μg/mL of the serum concentration of orticumab.

Figure 5:
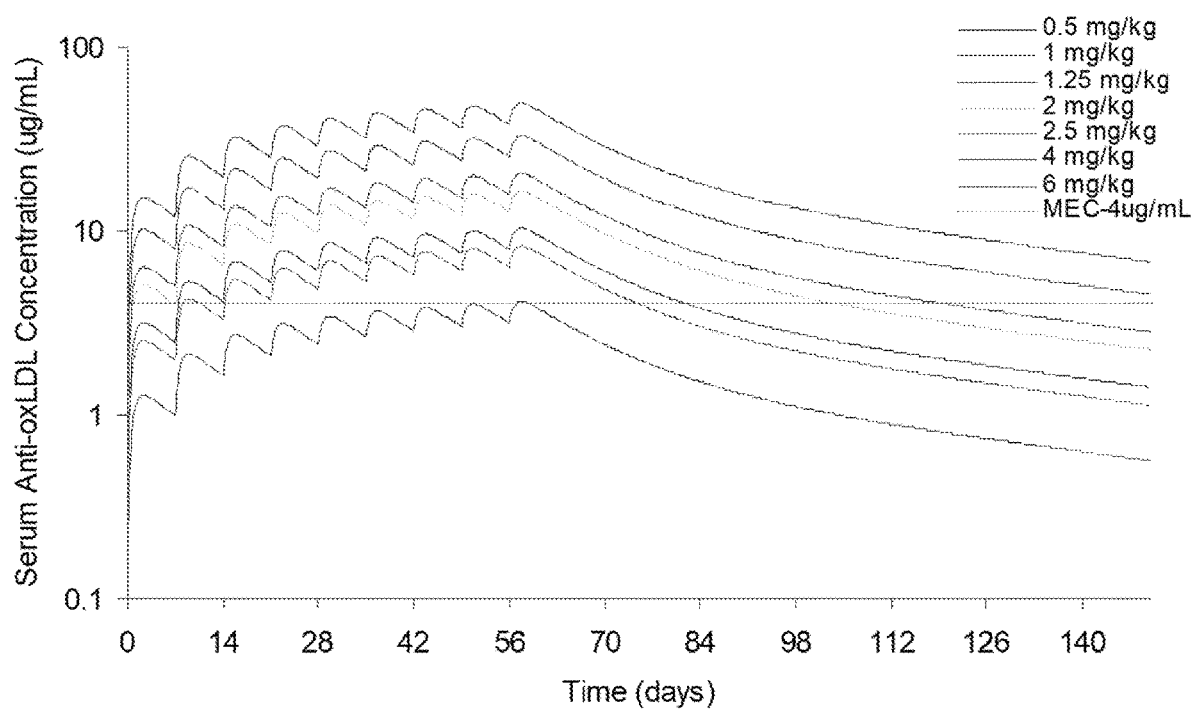

FIG. 5 depicts the simulated human PK profiles after weekly SC dosing, using PK parameters from Phase I data. The solid lines in the graph from low to high represent dosages at 0.5, 1, 1.25, 2, 2.5, 4 or 6 mg/kg.

Figure 6:
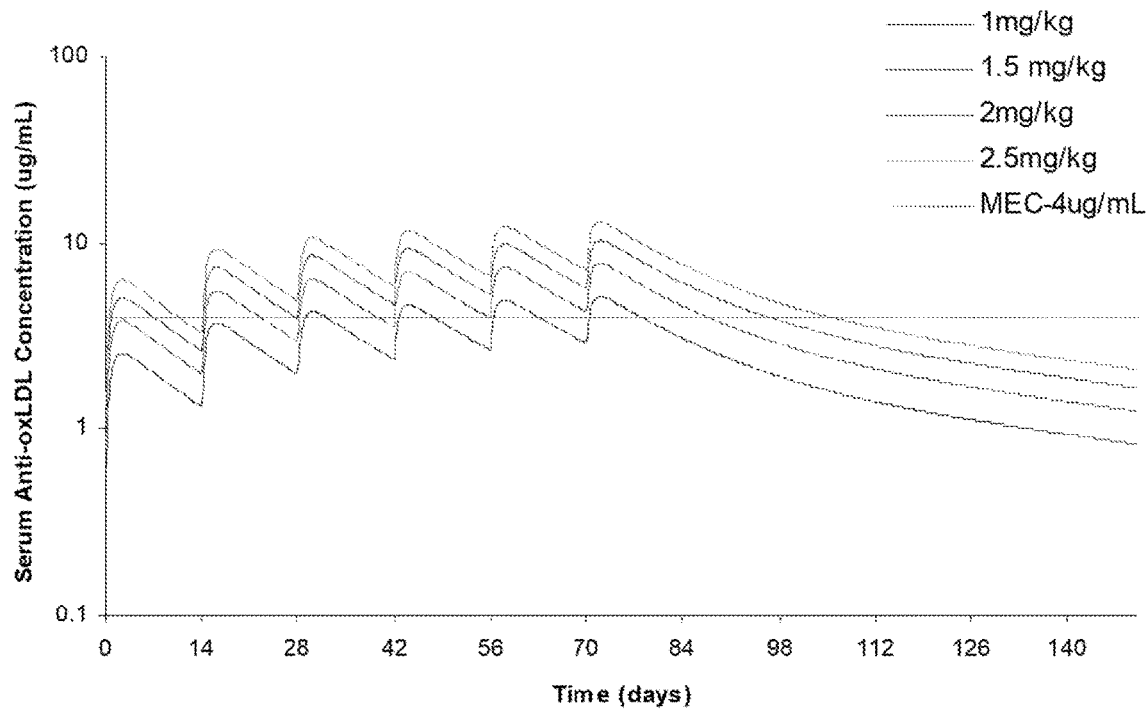

FIG. 6 depicts the simulated human PK profiles after bi-weekly SC dosing, using PK parameters from Phase I data. The solid lines in the graph from low to high represent dosages at 1, 1.5, 2 or 2.5 mg/kg.

Figure 7:
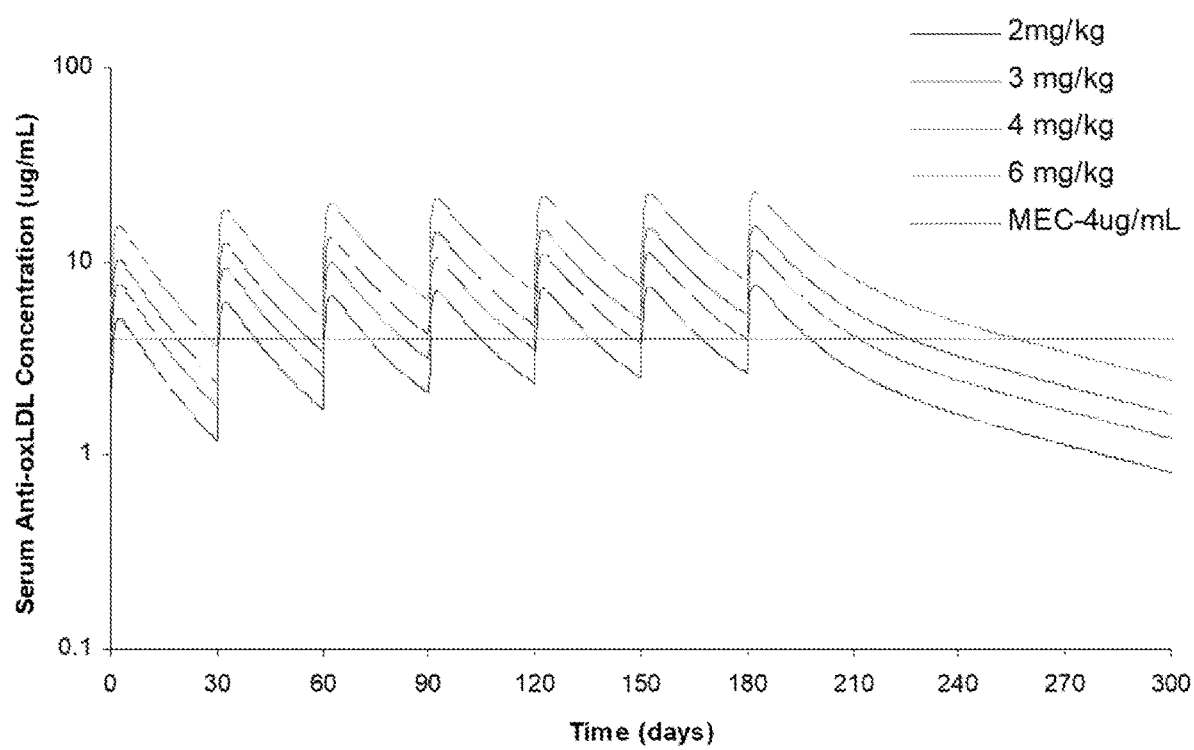

FIG. 7 depicts the simulated human PK profiles after monthly SC dosing, using parameters from Phase I data. The solid lines in the graph from low to high represent dosages at 2, 3, 4 or 6 mg/kg.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ *ed., Revised*, J. Wiley & Sons (New York, N.Y. 2006); March, *Advanced Organic Chemistry Reactions, Mechanisms and Structure* 7$^{th}$ *ed.*, J. Wiley & Sons (New York, N.Y. 2013); and Sambrook and Russel, *Molecular Cloning: A Laboratory Manual* 4$^{th}$ *ed.*, Cold Spring Harbor Laboratory Press (Cold Spring Harbor, N.Y. 2012), provide one skilled in the art with a general guide to many of the terms used in the present application. For references on how to prepare antibodies, see D. Lane, *Antibodies: A Laboratory Manual* 2$^{nd}$ *ed.* (Cold Spring Harbor Press, Cold Spring Harbor N.Y., 2013); Kohler and Milstein, (1976) Eur. J. Immunol. 6: 511; Queen et al. U.S. Pat. No. 5,585,089; and Riechmann et al., Nature 332: 323 (1988); U.S. Pat. No. 4,946,778; Bird, Science 242:423-42 (1988); Huston et al., Proc. Natl. Acad. Sci. USA 85:5879-5883 (1988); Ward et al., Nature 334:544-54 (1989); Tomlinson I. and Holliger P. (2000) Methods Enzymol, 326, 461-479; Holliger P. (2005) Nat. Biotechnol. September; 23(9):1126-36).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "antibody" or "antibodies" as used herein are meant in a broad sense and includes immunoglobulin molecules including polyclonal antibodies, monoclonal antibodies including murine, human, human-adapted, humanized and chimeric monoclonal antibodies, antibody fragments, bispecific or multispecific antibodies, dimeric, tetrameric or multimeric antibodies, and single chain antibodies.

Immunoglobulins can be assigned to five major classes, namely IgA, IgD, IgE, IgG and IgM, depending on the heavy chain constant domain amino acid sequence. IgA and IgG are further sub-classified as the isotypes IgA$_1$, IgA$_2$, IgG$_1$, IgG$_2$, IgG$_3$ and IgG$_4$. Antibody light chains of any vertebrate species can be assigned to one of two clearly distinct types, namely kappa (κ) and lambda (λ), based on the amino acid sequences of their constant domains.

The term "antibody fragment" refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region ($V_H$), or a light chain variable region ($V_L$). Antibody fragments include a Fab fragment, a monovalent fragment consisting of the $V_L$, $V_H$, CL and CHI domains; a F(ab)$_2$ fragment, a bivalent fragment comprising two Fab fragments linked by a disulfide bridge at the hinge region; a Fd fragment consisting of the $V_H$ and $C_{H1}$ domains; a Fv fragment consisting of the $V_L$ and $V_H$ domains of a single arm of an antibody; a domain antibody (dAb) fragment (Ward et al (1989) Nature 341:544-546), which consists of a $V_H$ domain. $V_H$ and $V_L$ domains can be engineered and linked together via a synthetic linker to form various types of single chain antibody designs where the $V_H/V_L$ domains pair intramolecularly, or intermolecularly in those cases when the $V_H$ and $V_L$ domains are expressed by separate single chain antibody constructs, to form a monovalent antigen binding site, such as single chain Fv (scFv) or diabody; described for example in PCT Intl. Publ. Nos. WO1998/44001, WO1988/01649, WO1994/13804, and WO1992/01047. These antibody fragments are obtained using well known techniques known to those of skill in the art, and the fragments are screened for utility in the same manner as are full length antibodies.

An antibody variable region consists of a "framework" region interrupted by three "antigen binding sites". The antigen binding sites are defined using various terms such as Complementarity Determining Regions (CDRs), three in the $V_H$ (HCDR1, HCDR2, HCDR3), and three in the $V_L$ (LCDR1, LCDR2, LCDR3), are based on sequence variability (Wu and Kabat J Exp Med 132:211-50, 1970; Kabat et al Sequences of Proteins of Immunological Interest, 5th Ed. Public Health Service, National Institutes of Health, Bethesda, Md., 1991) or "Hypervariable regions", "HVR", or "HV", three in the $V_H$ (H1, H2, H3) and three in the $V_L$ (L1, L2, L3), refer to the regions of an antibody variable domains which are hypervariable in structure as defined by Chothia and Lesk (Chothia and Lesk Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro, Mol Recognit 17:132-43, 2004). The International ImMunoGeneTics (IMGT) database provides a standardized numbering and definition of antigen-binding sites. The correspondence between CDRs, HVs and IMGT delineations is described in Lefranc et al., Dev Comparat Immunol 27:55-77, 2003.

"Framework" or "framework sequences" are the remaining sequences of a variable region other than those defined to be antigen binding sites. Because the antigen binding sites can be defined by various terms as described above, the exact amino acid sequence of a framework depends on how the antigen-binding site was defined.

"Humanized antibody" refers to an antibody in which the antigen binding sites are derived from non-human species and the variable region frameworks are derived from human immunoglobulin sequences. Humanized antibodies may include substitutions in the framework regions so that the framework may not be an exact copy of expressed human immunoglobulin or germline gene sequences.

"Human-adapted" antibodies or "human framework adapted (HFA)" antibodies refer to humanized antibodies adapted according to methods described in U.S. Pat. Publ. No. US2009/0118127. Human-adapted antibodies are humanized by selecting the acceptor human frameworks based on the maximum CDR and FR similarities, length compatibilities and sequence similarities of CDR1 and CDR2 loops and a portion of light chain CDR3 loops.

"Human antibody" refers to an antibody having heavy and light chain variable regions in which both the framework and the antigen binding sites are derived from sequences of human origin. If the antibody contains a constant region, the constant region also is derived from sequences of human origin.

A human antibody comprises heavy or light chain variable regions that are "derived from" sequences of human origin wherein the variable regions of the antibody are obtained from a system that uses human germline immunoglobulin or rearranged immunoglobulin genes. Such systems include human immunoglobulin gene libraries displayed on phage, and transgenic non-human animals such as mice carrying human immunoglobulin loci as described herein. A "human antibody" may contain amino acid differences when compared to the human germline or rearranged immunoglobulin sequences due to for example naturally occurring somatic mutations or intentional introduction of substitutions in the framework or antigen binding sites. Typically, a human antibody is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, "human antibody" may contain consensus framework sequences derived from human framework sequence analyses, for example as described in Knappik et al., J Mol Biol 296:57-86, 2000), or synthetic HCDR3 incorporated into human immunoglobulin gene libraries displayed on phage, for example as described in Shi et al., J Mol Biol 397:385-96, 2010 and Intl. Pat. Publ. No. WO2009/085462. Antibodies in which antigen binding sites are derived from a non-human species are not included in the definition of human antibody.

The term "recombinant antibody" as used herein, includes all antibodies that are prepared, expressed, created or isolated by recombinant means, such as antibodies isolated from an animal (e.g., a mouse) that is transgenic or transchromosomal for human immunoglobulin genes or a hybridoma prepared therefrom (described further below), antibodies isolated from a host cell transformed to express the antibody, antibodies isolated from a recombinant, combinatorial antibody library, and antibodies prepared, expressed, created or isolated by any other means that involve splicing of human immunoglobulin gene sequences to other DNA sequences, or antibodies that are generated in vitro using Fab arm exchange such as bispecific antibodies.

The term "monoclonal antibody" as used herein refers to a preparation of antibody molecules of single molecular composition. A monoclonal antibody composition displays a single binding specificity and affinity for a particular epitope, or in a case of a bispecific monoclonal antibody, a dual binding specificity to two distinct epitopes.

The term "epitope" as used herein means a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Variant" as used herein refers to a polypeptide or a polynucleotide that differs from a reference polypeptide or a reference polynucleotide by one or more modifications for example, substitutions, insertions or deletions.

"Administering" and/or "administer" as used herein refer to any route for delivering a pharmaceutical composition to a patient. Routes of delivery may include non-invasive peroral (through the mouth), topical (skin), transmucosal (nasal, buccal/sublingual, vaginal, ocular and rectal) and inhalation routes, as well as parenteral routes, and other methods known in the art. Parenteral refers to a route of delivery that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, sub arachnoid, subcapsular, subcutaneous, transmucosal, or transtracheal. Via the parenteral route, the compositions may be in the form of solutions or suspensions for infusion or for injection, or as lyophilized powders.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and/or prolonging a patient's life or life expectancy. In some embodiments, the disease condition is rheumatoid arthritis, or a combination of rheumatoid arthritis and accelerated atherosclerosis.

The term "effective amount" as used herein refers to the amount of a pharmaceutical composition comprising one or more antibody or antibody fragment as disclosed herein or a mutant, variant, analog or derivative thereof, to decrease at least one or more symptom of the disease or disorder, and relates to a sufficient amount of pharmacological composition to provide the desired effect. The phrase "therapeutically effective amount" as used herein means a sufficient amount of the composition to treat a disorder, at a reasonable benefit/risk ratio applicable to any medical treatment. In various embodiments, the pharmaceutical compositions described herein further comprise a pharmaceutically acceptable carrier. In some embodiments, a therapeutic pharmaceutical composition is used, for example, to treat, inhibit, reduce the severity of and/or, reduce duration of rheumatoid arthritis, or a combination of rheumatoid arthritis and accelerated atherosclerosis, and/or related symptoms in a subject in need thereof.

A therapeutically or prophylactically significant reduction in a symptom is, e.g., at least 5%, at least 10%, at least 20%, at least 30%, at least 40%, at least 50%, at least 60%, at least 70%, at least 80%, at least 90%, at least 100%, or more in a measured parameter as compared to a control or non-treated subject or the state of the subject prior to administering the compositions described herein. Measured or measurable parameters include clinically detectable markers of disease, for example, elevated or depressed levels of a biological marker, as well as parameters related to a clinically accepted scale of symptoms or markers for rheumatoid arthritis and/or accelerated atherosclerosis. It will be understood, however, that the total daily usage of the compositions and formulations as disclosed herein will be decided by the attending physician within the scope of sound medical judgment. The exact amount required will vary depending on factors such as the type of disease being treated, gender, age, and weight of the subject. "Ineffective" treatment refers to when a subject is administered a treatment and there is less than 1%, 2%, 3%, 4% or 5%, improvement in symptoms.

"Subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease-state is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

The term "statistically significant" or "significantly" refers to statistical evidence that there is a difference. It is defined as the probability of making a decision to reject the null hypothesis when the null hypothesis is actually true. The decision is often made using the p-value.

"Bind" in reference to the interaction between antibody and epitope, "selectively binds" or "specifically binds" refers to the ability of an antibody or antibody fragment thereof described herein to bind to a target, such as a molecule present on the cell-surface, with a $K_D$ $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay.

The term "in combination with" as used herein means that two or more therapeutics can be administered to a subject together in a mixture, concurrently as single agents or sequentially as single agents in any order.

A "cardiovascular disease," as used herein, refers to a disorder of the heart and blood vessels, and includes disorders of the arteries, veins, arterioles, venules, and capillaries. Non-limiting examples of cardiovascular diseases include congestive heart failure, arrhythmia, pericarditis, acute myocardial infarction, infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, atrial fibrillation, congenital heart disease, endocarditis, inflammatory heart disease, endocarditis, inflammatory cardiomegaly, myocarditis, valvular heart disease, cerebrovascular disease, and peripheral artery disease, or any combination thereof.

"Rheumatoid arthritis" is an autoimmune disease in which the body's immune system—which normally protects its health by attacking foreign substances like bacteria and viruses—mistakenly attacks the joints. This creates inflammation that causes the tissue that lines the inside of joints (the synovium) to thicken, resulting in swelling and pain in and around the joints. The synovium makes a fluid that lubricates joints and helps them move smoothly. Rheumatoid arthritis most commonly affects the joints of the hands, feet, wrists, elbows, knees and ankles. The joint effect is usually symmetrical. That means if one knee or hand if affected, usually the other one is, too. Because RA also can affect body systems, such as the cardiovascular or respiratory systems, it is called a systemic disease. Symptoms of rheumatoid arthritis include, but are not limited to, joint pain, tenderness, swelling or stiffness for six weeks or longer; morning stiffness for 30 minutes or longer; more than one joint is affected; small joints (wrists, certain joints of the hands and feet) are affected; and the same joints on both sides of the body are affected.

"Arthritis" is inflammation of one or more of your joints. Two most common types of arthritis are osteoarthritis and rheumatoid arthritis. Osteoarthritis causes cartilage—the hard, slippery tissue that covers the ends of bones where they form a joint—to break down. Rheumatoid arthritis is an autoimmune disorder that first targets the lining of joints (synovium). Uric acid crystals, infections or underlying disease, such as rheumatoid arthritis, accelerated atherosclerosis, or both.

Generally, two types of atherosclerosis were described, spontaneous and accelerated. The development of atherosclerosis is accelerated in patients with rheumatoid arthritis (RA) and other forms of inflammatory arthritis or rheumatologic conditions. With accelerated atherosclerosis, a patient presents earlier, and may develop more quickly, atherosclerotic lesions, compared to non-diseased age matched controls.

Methods and Systems

Various embodiments provide a method of treating or reducing the severity of rheumatoid arthritis, accelerated atherosclerosis, or both in a subject by administering to the subject an antibody or antibody fragment that binds to at least one fragment of apolipoprotein B100 (apoB100). In one aspect, the method treats or reduces the severity of rheumatoid arthritis in a subject by administering to the subject an antibody or antibody fragment that binds to at least one fragment of apolipoprotein B100 (apoB100). In another aspect, the method treats or reduces the severity of accelerated atherosclerosis in a subject by administering to the subject an antibody or antibody fragment that binds to at least one fragment of apolipoprotein B100 (apoB100). In yet another aspect, the method treats or reduces the severity of both rheumatoid arthritis and accelerated atherosclerosis in a subject by administering to the subject an antibody or antibody fragment that binds to at least one fragment of apolipoprotein B100 (apoB100). In yet another aspect, the method treats or reduces the severity of accelerated atherosclerosis in a subject exhibiting symptoms or having been diagnosed with rheumatoid arthritis by administering to the subject an antibody or antibody fragment that binds to at least one fragment of apolipoprotein B100 (apoB100).

Various embodiments provide a method of reducing the likelihood of having rheumatoid arthritis, accelerated atherosclerosis, or both in a subject by administering to the subject an antibody or antibody fragment that binds to at least one fragment of apolipoprotein B100 (apoB100). In various embodiments, the method provides passive immunity to the subject to reduce the likelihood of developing rheumatoid arthritis in a subject, or accelerated atherosclerosis in a subject with rheumatoid arthritis.

Various embodiments provide the antibody or antibody fragment in the methods disclosed herein binds to a native and/or an oxidized epitope P45 of apoB100. Various embodiments provide the antibody or antibody fragment in the methods disclosed herein only binds to a native and/or an oxidized epitope P45 of apoB100. P45 of apoB100 has a polypeptide sequence of IEIGLEGKGFEPTLEALFGK (SEQ ID No.: 1). An oxidized epitope or oxidized lipoprotein includes but is not limited to a modification on the epitope or lipoprotein to carry malone-di-aldehyde (MDA) groups on lysines and histidines, a modification that is induced by oxidation by copper (e.g., CuOxLDL), a modification to carry hydroxynonenal, or a modification to carry a hapten of an aldehyde. Another embodiment provides the antibody or antibody fragment in the method disclosed herein further binds one or more fragments of apoB100.

ApoB100 contains peptide fragments that can be identified as P1-P302, which have overlapping amino acids between adjacent peptides, as described in U.S. patent application publication no. US/2017/0340702 and U.S. Pat. Nos. 7,468,183 and 7,704,499, which are incorporated by reference herein in their entireties.

Various embodiments provide that the method of treating or reducing the severity of rheumatoid arthritis, accelerated atherosclerosis, or both in a subject, or treating or reducing the severity of accelerated atherosclerosis in a subject with rheumatoid arthritis, includes but is not limited to administering orticumab or a variant of orticumab that has identical heavy chain and/or light chain to those of orticumab, or identical complementarity determining regions to those of orticumab, which is also detailed below.

Various embodiments provide that the method of reducing the likelihood of rheumatoid arthritis, accelerated atherosclerosis, or both in a subject, or reducing the likelihood of developing accelerated atherosclerosis in a subject with rheumatoid arthritis, includes but is not limited to administering orticumab or a variant of orticumab that has identical heavy chain and/or light chain to those of orticumab, or identical complementarity determining regions to those of orticumab, which is also detailed below. In further aspect, the method provides passive immunity to the subject to reduce the likelihood of having rheumatoid arthritis, accelerated atherosclerosis, or both.

Various embodiments of any one or more of the methods disclosed herein include that the subject after the treatment has reduced levels of one or more of inflammation markers including MCP-1, TNFα, IL-1β, IL-6 and CRP, compared to before the treatment, by at least 5%, at least 10%, at least 15%, at least 20%, or at least 25%. Other embodiments provide any one or more of the methods disclosed herein include that the subject after the treatment has reduced joint pain, swelling or stiffness, and/or plaque areas. Further embodiments provide that the disclosed methods of treating or reducing the severity or the likelihood of rheumatoid arthritis in a subject result in the reduced levels of one, two, three, four or five of the inflammation markers from the group of MCP-1, TNFα, IL-1β, IL-6 and CRP. Yet further embodiments provide that the disclosed methods of treating or reducing the severity or the likelihood of accelerated atherosclerosis in a subject with rheumatoid arthritis result in the reduced levels of one, two, three, four or five of the inflammation markers from the group of MCP-1, TNFα, IL-1β, IL-6 and CRP. Yet further embodiments provide that the disclosed methods of treating or reducing the severity of both rheumatoid arthritis and accelerated atherosclerosis in a subject result in the reduced levels of one, two, three, four or five of the inflammation markers from the group of MCP-1, TNFα, IL-1β, IL-6 and CRP.

The methods resulting in reduced levels of "one or more of MCP-1, TNFα, IL-1β, IL-6 and CRP" encompass embodiments of reducing one, two, three, four, or all five of the inflammation markers, compared to that before the treatment. For example, one aspect provides that the methods result in a reduced level of MCP-1. One aspect provides that the methods result in a reduced level of TNFα. One aspect provides that the methods result in a reduced level of IL-1β. One aspect provides that the methods result in a reduced level of IL-6. One aspect provides that the methods result in a reduced level of CRP. Another aspect provides that the methods result in a reduced level of MCP-1 and TNFα. Another aspect provides that the methods result in a reduced level of MCP-1 and IL-1β. Another aspect provides that the methods result in a reduced level of MCP-1 and IL-6. Another aspect provides that the methods result in a reduced level of MCP-1 and CRP. Another aspect provides that the methods result in a reduced level of TNFα and IL-1β. Another aspect provides that the methods result in a reduced level of TNFα and IL-6. Another aspect provides that the methods result in a reduced level of TNFα and CRP. Another aspect provides that the methods result in a reduced level of IL-1β and IL-6. Another aspect provides that the methods result in a reduced level of IL-1β and CRP. Another aspect provides that the methods result in a reduced level of IL-6 and CRP. Yet another aspect provides that the methods result in a reduced level of MCP-1, TNFα and IL-1β. Another aspect provides that the methods result in a reduced level of MCP-1, TNFα and IL-6. Another aspect provides that the methods result in a reduced level of MCP-1, TNFα and CRP. Another aspect provides that the methods result in a reduced level of MCP-1, IL-1β and IL-6. Another aspect provides that the methods result in a reduced level of MCP-1, IL-1β and CRP. Another aspect provides that the methods result in a reduced level of MCP-1, IL-6 and CRP. Another aspect provides that the methods result in a reduced level of TNFα, IL-1β and IL-6. Another aspect provides that the methods result in a reduced level of TNFα, IL-1β and CRP. Another aspect provides that the methods result in a reduced level of TNFα, IL-6 and CRP. Another aspect provides that the methods result in a reduced level of IL-1β, IL-6 and CRP. Another aspect provides that the methods result in a reduced level of MCP-1, TNFα, IL-1β and IL-6. Another aspect provides that the methods result in a reduced level of MCP-1, TNFα, IL-1β and CRP. Another aspect provides that the methods result in a reduced level of MCP-1, TNFα, IL-6 and CRP. Another aspect provides that the methods result in a reduced level of MCP-1, IL-1β, IL-6 and CRP. Another aspect provides that the methods result in a reduced level of TNFα, IL-1β, IL-6 and CRP. Yet another aspect provides that the methods result in a reduced level of MCP-1, TNFα, IL-1β, IL-6 and CRP.

Orticumab is a human monoclonal antibody that contains heavy chain complementarity determining regions (HCDR) 1 (HCDR1), 2 (HCDR2) and 3 (HCDR3) as set forth in SEQ ID Nos: 2, 3 and 4, respectively; and light chain complementarity determining regions (LCDR) 1 (LCDR1), 2 (LCDR2) and 3 (LCDR3) as set forth in SEQ ID Nos: 5, 6 and 7, respectively. Orticumab contains a variable heavy region ($V_H$) amino acid sequence of SEQ ID No: 8, a variable light region ($V_L$) amino acid sequence of SEQ ID No: 9. Orticumab contains a heavy chain amino acid sequence of SEQ ID No: 10, a light chain amino acid sequence of SEQ ID No: 11.

```
EVQLLESGGG LVQPGGSLRL SCAASGFTFS NAWMSWVRQA
PGKGLEWVSS ISVGGHRTYY ADSVKGRSTI SRDNSKNTLY
LQMNSLRAED TAVYYCARIR VGPSGGAFDY WGQGTLVTVS.
```

Variable light region ($V_L$), i.e., SEQ ID No.: 9, is as shown:

```
QSVLTQPPSA SGTPGQRVTI SCSGSNTNIG KNYVSWYQQL
PGTAPKLLIY ANSNRPSGVP DRFSGSKSGT SASLAISGLR
SEDEADYYCA SWDASLNGWV FGGGTKLTVL.
```

Heavy chain, i.e., SEQ ID No.:10, is as shown:

```
EVQLLESGGG LVQPGGSLRL SCAASGFTFS NAWMSWVRQA

PGKGLEWVSS ISVGGHRTYY ADSVKGRSTI SRDNSKNTLY

LQMNSLRAED TAVYYCARIR VGPSGGAFDY WGQGTLVTVS

SASTKGPSVI PLAPSSKSTS GGTAALGCLV KDYFPEPVTV

SWNSGALTSG VHTFPAVLQS SGLYSLSSVV TVPSSSLGTQ

TYICNVNHKP SNTKVDKKVE PKSCDKTHTC PPCPAPELLG

GPSVFLFPPK PKDTLMISRT PEVTCVVVDV SHEDPEVKFN

WYVDGVEVHN AKTKPREEQY NSTYRVVSVL TVLHQDWLNG

KEYKCKVSNK ALPAPIEKTI SKAKGQPREP QVYTLPPSRD

ELTKNQVSLT CLVKGFYPSD IAVEWESNGQ PENNYKTTPP

VLDSDGSFFL YSKLTVDKSR WQQGNVFSCS VMHEALHNHY

TQKSLSLSPG K.
```

Light chain, i.e., SEQ ID No.:11, is as shown:

```
QSVLTQPPSA SGTPGQRVTI SCSGSNTNIG KNYVSWYQQL

PGTAPKLLIY ANSNRPSGVP DRFSGSKSGT SASLAISGLR

SEDEADYYCA SWDASLNGWV FGGGTKLTVL GQPKAAPSVT

LFPPSSEELQ ANKATLVCLI SDFYPGAVTV AWKADSSPVK

AGVETTTPSK QSNNKYAASS YLSLTPEQWK SHRSYSCQVT

HEGSTVEKTV APTECS.
```

Methods are provided of treating or reducing the severity of rheumatoid arthritis, accelerated atherosclerosis, or both in a subject, or treating or reducing the severity of accelerated atherosclerosis in a subject with rheumatoid arthritis, including administering to the subject an effective amount of an antibody or antibody fragment that binds a fragment set forth in SEQ ID No.: 1 of apoB100, and the antibody contains one or more of HCDR1, HCDR2, HCDR3, LCDR1, LCDR2 and LCDR3 as set forth in SEQ ID Nos.: 2-7, respectively.

Methods of treating or reducing the likelihood of developing rheumatoid arthritis, accelerated atherosclerosis, or both in a subject, or reducing the likelihood of accelerated atherosclerosis in a subject with rheumatoid arthritis, are also provided including administering to the subject an effective amount of an antibody or antibody fragment that binds a fragment set forth in SEQ ID No.: 1 of apoB100, and the antibody contains one or more of HCDR1, HCDR2, HCDR3, LCDR1, LCDR2 and LCDR3 as set forth in SEQ ID Nos.: 2-7, respectively.

The antibody containing "one or more of HCDR1, HCDR2, HCDR3, LCDR1, LCDR2 and LCDR3" encompasses embodiments that the antibody contains one, two, three, four, five or all six of the CDRs (i.e., HCDR1, HCDR2, HCDR3, LCDR1, LCDR2 and LCDR3). One aspect of the invention provides an antibody comprising at least one complementarity determining region (CDR) that has the amino acid sequence of the corresponding CDR of antibody orticumab; that more preferably, the antibody has two or three or four or five CDRs that have the sequence of the corresponding CDRs of antibody orticumab; that if the antibody has three or four CDRs that have the sequence of the corresponding CDRs of antibody orticumab, it is preferred if the antibody has all three heavy chain or all three light chain CDRs that have the sequence of the corresponding CDRs of antibody orticumab; that thus this aspect of the invention includes an antibody comprising three light chain CDRs that have the sequence of the corresponding three light chain CDRs of antibody orticumab, or three heavy chain CDRs that have the sequence of the corresponding three heavy chain CDRs of antibody orticumab; that yet more preferably, the antibody comprises three light chain CDRs and three heavy chain CDRs that have the sequence of the corresponding CDRs of antibody orticumab; that if the antibody does not comprise all six CDRs that have the sequence of the corresponding CDRs of antibody orticumab, it is preferred if some or all of the 1, 2, 3, 4 or 5 "non-identical" CDRs comprise a variant of the sequence of the corresponding CDRs of antibody orticumab, (by "a variant" we includes the meaning that the variant has at least 50% sequence identity with the sequence of the corresponding CDR, more preferably at least 70%, yet more preferably at least 80% or at least 90% or at least 95%; most preferably, the variant has 96% or 97% or 98% or 99% sequence identity with the sequence of the corresponding CDR of antibody orticumab; typically the "variant" CDR sequence has 5 or 4 or 3 or 2 or only 1 amino acid residue difference from the sequence of the corresponding CDR of antibody orticumab); and that this aspect of the invention includes antibody orticumab. For example, one aspect of the embodiment provides that the administered antibody contains HCDR1 as set forth in SEQ ID No.: 2. Another aspect provides that the administered antibody contains HCDR2 as set forth in SEQ ID No.: 3. Another aspect provides that the administered antibody contains HCDR3 as set forth in SEQ ID No.: 4. Yet another aspect provides that the administered antibody contains LCDR1 as set forth in SEQ ID No.: 5. Another aspect provides that the administered antibody contains LCDR2 as set forth in SEQ ID No.: 6. Another aspect provides that the administered antibody contains LCDR3 as set forth in SEQ ID No.:7. Yet another aspect provides that the administered antibody contains HCDR1 as set forth in SEQ ID No.:2 and HCDR2 as set forth in SEQ ID No.: 3. Another aspect provides that the administered antibody contains HCDR1 as set forth in SEQ ID No.:2 and HCDR3 as set forth in SEQ ID No.: 4. Another aspect provides that the administered antibody contains HCDR1 as set forth in SEQ ID No.:2 and LCDR1 as set forth in SEQ ID No.: 5. Another aspect provides that the administered antibody contains HCDR1 as set forth in SEQ ID No.:2 and LCDR2 as set forth in SEQ ID No.: 6. Another aspect provides that the administered antibody contains HCDR1 as set forth in SEQ ID No.:2 and LCDR3 as set forth in SEQ ID No.: 7. Another aspect provides that the administered antibody contains HCDR2 as set forth in SEQ ID No.:3 and HCDR3 as set forth in SEQ ID No.: 4. Another aspect provides that the administered antibody contains HCDR2 as set forth in SEQ ID No.:3 and LCDR1 as set forth in SEQ ID No.: 5. Another aspect provides that the administered antibody contains HCDR2 as set forth in SEQ ID No.:3 and LCDR2 as set forth in SEQ ID No.: 6. Another aspect provides that the administered antibody contains HCDR2 as set forth in SEQ ID No.:3 and LCDR3 as set forth in SEQ ID No.: 7. Another aspect provides that the administered antibody contains HCDR3 as set forth in SEQ ID No.:4 and LCDR1 as set forth in SEQ ID No.: 5. Another aspect provides that the administered antibody contains HCDR3 as set forth in SEQ ID No.:4 and LCDR2 as set forth in SEQ ID No.: 6. Another aspect provides that the administered antibody contains HCDR3 as set forth in SEQ ID No.:4 and LCDR3 as set forth in SEQ ID No.: 7. Another aspect provides that the administered antibody contains LCDR1 as set forth in SEQ ID No.:5 and LCDR2 as set forth in SEQ ID No.: 6. Another aspect provides that the administered antibody contains LCDR1 as set forth in SEQ ID No.:5 and LCDR3 as set forth in SEQ ID No.: 7. Another aspect provides that the administered antibody contains LCDR2 as set forth in SEQ ID No.:6 and LCDR3 as set forth in SEQ ID No.: 7. Another aspect provides that the administered antibody contains HCDR1, HCDR2 and HCDR3 as set forth in SEQ ID Nos.: 2-4, respectively. Another aspect provides that the administered antibody contains HCDR1, HCDR2 and LCDR1 as set forth in SEQ ID Nos.: 2, 3 and 5, respectively. Another aspect provides that the administered antibody contains HCDR1, HCDR2 and LCDR2 as set forth in SEQ ID Nos.: 2, 3 and 6, respectively. Another aspect provides that the administered antibody contains HCDR1, HCDR2 and LCDR3 as set forth in SEQ ID Nos.: 2, 3 and 7, respectively. Another aspect provides that the administered antibody contains HCDR1, HCDR3 and LCDR1 as set forth in SEQ ID Nos.: 2, 4 and 5, respectively. Another aspect provides that the administered antibody contains HCDR1, HCDR3 and LCDR2 as set forth in SEQ ID Nos.: 2, 4 and 6, respectively. Another aspect provides that the administered antibody contains HCDR1, HCDR3 and LCDR3 as set forth in SEQ ID Nos.: 2, 4 and 7, respectively. Another aspect provides that the administered antibody contains HCDR1, LCDR1 and LCDR2 as set forth in SEQ ID Nos.: 2, 5 and 6, respectively. Another aspect provides that the administered antibody contains HCDR1, LCDR1 and LCDR3 as set forth in SEQ ID Nos.: 2, 5 and 7, respectively. Another aspect provides that the administered antibody contains HCDR1, LCDR2 and LCDR3 as set forth in SEQ ID Nos.: 2, 6 and 7, respectively. Another aspect provides that the administered antibody contains HCDR2, HCDR3 and LCDR1 as set forth in SEQ ID Nos.: 3, 4 and 5, respectively. Another aspect provides that the administered antibody contains HCDR2, HCDR3 and LCDR2 as set forth in SEQ ID Nos.: 3, 4 and 6, respectively. Another aspect provides that the administered antibody contains HCDR2, HCDR3 and LCDR3 as set forth in SEQ ID Nos.: 3, 4 and 7, respectively. Another aspect provides that the administered antibody contains HCDR2, LCDR1 and LCDR2 as set forth in SEQ ID Nos.: 3, 5 and 6, respectively. Another aspect provides that the administered antibody contains HCDR2, LCDR1 and LCDR3 as set forth in SEQ ID Nos.: 3, 5 and 7, respectively. Another aspect provides that the administered antibody contains HCDR2, LCDR2 and LCDR3 as set forth in SEQ ID Nos.: 3, 6 and 7, respectively. Another aspect provides that the administered antibody contains HCDR3, LCDR1 and LCDR2 as set forth in SEQ ID Nos.:4, 5 and 6, respectively. Another aspect provides that the administered antibody contains HCDR3, LCDR1 and LCDR3 as set forth in SEQ ID Nos.:4, 5 and 7, respectively. Another aspect provides that the administered antibody contains HCDR3, LCDR2 and LCDR3 as set forth in SEQ ID Nos.:4, 6 and 7, respectively. Another aspect provides that the administered antibody contains LCDR1, LCDR2 and LCDR3 as set forth in SEQ ID Nos.:5-7, respectively. Yet another aspect provides that the administered antibody contains HCDR1, HCDR2, HCDR3 and LCDR1 as set forth in SEQ ID Nos.:2-5, respectively. Another aspect provides that the administered antibody contains HCDR1, HCDR2, HCDR3 and LCDR2 as set forth in SEQ ID Nos.:2-4 and 6, respectively. Another aspect provides that the administered antibody contains HCDR1, HCDR2, HCDR3 and LCDR3 as set forth in SEQ ID Nos.:2-4 and 7, respectively. Another aspect provides that the administered antibody contains HCDR1, HCDR2, LCDR1 and LCDR2 as set forth in SEQ ID Nos.:2, 3, 5 and 6, respectively. Another aspect provides that the administered antibody contains HCDR1, HCDR2, LCDR1 and LCDR3 as set forth in SEQ ID Nos.:2, 3, 5 and 7, respectively. Another aspect provides that the administered antibody contains HCDR1, HCDR2, LCDR2 and LCDR3 as set forth in SEQ ID Nos.:2, 3, 6 and 7, respectively. Another aspect provides that the administered antibody contains HCDR1, HCDR3, LCDR1 and LCDR2 as set forth in SEQ ID Nos.:2, 4, 5 and 6, respectively. Another aspect provides that the administered antibody contains HCDR1, HCDR3, LCDR1 and LCDR3 as set forth in SEQ ID Nos.:2, 4, 5 and 7, respectively. Another aspect provides that the administered antibody contains HCDR1, HCDR3, LCDR2 and LCDR3 as set forth in SEQ ID Nos.:2, 4, 6 and 7, respectively. Another aspect provides that the administered antibody contains HCDR1, LCDR1, LCDR2 and LCDR3 as set forth in SEQ ID Nos.:2, 5, 6 and 7, respectively. Another aspect provides that the administered antibody contains HCDR2, HCDR3, LCDR1 and LCDR2 as set forth in SEQ ID Nos.:3-6, respectively. Another aspect provides that the administered antibody contains HCDR2, HCDR3, LCDR1 and LCDR3 as set forth in SEQ ID Nos.:3-5 and 7, respectively. Another aspect provides that the administered antibody contains HCDR2, HCDR3, LCDR2 and LCDR3 as set forth in SEQ ID Nos.:3, 4, 6 and 7, respectively. Another aspect provides that the administered antibody contains HCDR2, LCDR1, LCDR2 and LCDR3 as set forth in SEQ ID Nos.:3, 5, 6 and 7, respectively. Another aspect provides that the administered antibody contains HCDR3, LCDR1, LCDR2 and LCDR3 as set forth in SEQ ID Nos.:4, 5, 6 and 7, respectively. Yet another aspect provides that the administered antibody contains HCDR1, HCDR2, HCDR3, LCDR1 and LCDR2 as set forth in SEQ ID Nos.: 2-6 respectively. Another aspect provides that the administered antibody contains HCDR1, HCDR2, HCDR3, LCDR1 and LCDR3 as set forth in SEQ ID Nos.: 2-5 and 7 respectively. Another aspect provides that the administered antibody contains HCDR1, HCDR2, HCDR3, LCDR2 and LCDR3 as set forth in SEQ ID Nos.: 2, 3, 4, 6 and 7 respectively. Another aspect provides that the administered antibody contains HCDR1, HCDR2, LCDR1, LCDR2 and LCDR3 as set forth in SEQ ID Nos.: 2, 3, 5-7, respectively. Another aspect provides that the administered antibody contains HCDR1, HCDR3, LCDR1, LCDR2 and LCDR3 as set forth in SEQ ID Nos.: 2, 4-7, respectively. Another aspect provides that the administered antibody contains HCDR2, HCDR3, LCDR1, LCDR2 and LCDR3 as set forth in SEQ ID Nos.: 3-7, respectively. Yet another aspect provides that the administered antibody contains HCDR1, HCDR2, HCDR3, LCDR1, LCDR2 and LCDR3 as set forth in SEQ ID Nos.: 2-7, respectively.

A further aspect of the invention provides that the method of treating, reducing the severity of rheumatoid arthritis, accelerated atherosclerosis, or both, or providing passive immunity to a subject against rheumatoid arthritis, accelerated atherosclerosis, or both, or treating or reducing the severity or likelihood of accelerated atherosclerosis in a subject with rheumatoid arthritis, consists of administering to the subject an effective amount of an antibody or antibody fragment that binds a fragment set forth in SEQ ID No.: 1 of apoB100, and the antibody contains HCDR1, HCDR2, HCDR3, LCDR1, LCDR2 and LCDR3 as set forth in SEQ ID Nos.: 2-7, respectively.

Methods are provided of treating or reducing the severity of rheumatoid arthritis, accelerated atherosclerosis, or both, or treating or reducing the severity of accelerated atherosclerosis in a subject with rheumatoid arthritis, including administering to the subject an effective amount of an antibody or antibody fragment that binds a fragment set forth in SEQ ID No.: 1 of apoB100, and the antibody contains a variable heavy region ($V_H$) as set forth in SEQ ID No.: 8 and a variable light region ($V_L$) containing LCDR1, LCDR2 and LCDR3 as set forth in SEQ ID Nos.: 5-7, respectively. A further aspect provides that the method of treating or reducing the severity of rheumatoid arthritis, accelerated atherosclerosis, or both, and/or providing passive immunity, or treating or reducing the severity of accelerated atherosclerosis in a subject with rheumatoid arthritis, includes administering to the subject an effective amount of an antibody or antibody fragment that binds a fragment set forth in SEQ ID No.: 1 of apoB100, and the antibody contains a variable light region ($V_L$) of SEQ ID No.: 9 and a variable heavy region ($V_H$) that contains HCDR1, HCDR2 and HCDR3 as set forth in SEQ ID Nos.: 2-4, respectively. Yet another aspect of the invention provides that the method of treating, reducing the severity of rheumatoid arthritis, accelerated atherosclerosis, or both, and/or reducing the likelihood of rheumatoid arthritis, accelerated atherosclerosis, or both in a subject, or treating or reducing the severity or likelihood of accelerated atherosclerosis in a subject with rheumatoid arthritis, includes administering to the subject an effective amount of an antibody or antibody fragment that binds a fragment set forth in SEQ ID No.: 1 of apoB100, and the antibody contains a variable heavy region ($V_H$) of SEQ ID No.: 8 and a variable light region ($V_L$) of SEQ ID No.: 9.

Methods are provided of reducing the likelihood of rheumatoid arthritis, accelerated atherosclerosis, or both, or providing passive immunity to a subject against rheumatoid arthritis, accelerated atherosclerosis, or both, or treating or reducing the severity or likelihood of accelerated atherosclerosis in a subject with rheumatoid arthritis, including administering to the subject an effective amount of an antibody or antibody fragment that binds a fragment set forth in SEQ ID No.: 1 of apoB100, and the antibody contains a variable heavy region ($V_H$) as set forth in SEQ ID No.: 8 and a variable light region ($V_L$) containing LCDR1, LCDR2 and LCDR3 as set forth in SEQ ID Nos.: 5-7, respectively. A further aspect provides that the method of treating, reducing the severity of rheumatoid arthritis, accelerated atherosclerosis, or both, and/or reducing the likelihood of rheumatoid arthritis, accelerated atherosclerosis, or both, in a subject includes administering to the subject an effective amount of an antibody or antibody fragment that binds a fragment set forth in SEQ ID No.: 1 of apoB100, and the antibody contains a variable light region ($V_L$) of SEQ ID No.: 9 and a variable heavy region ($V_H$) that contains HCDR1, HCDR2 and HCDR3 as set forth in SEQ ID Nos.: 2-4, respectively. Yet another aspect of the invention provides that the method of treating, reducing the severity of rheumatoid arthritis, accelerated atherosclerosis, or both, and/or reducing the likelihood of having rheumatoid arthritis, accelerated atherosclerosis, or both in a subject, or treating or reducing the severity or likelihood of accelerated atherosclerosis in a subject with rheumatoid arthritis, includes administering to the subject an effective amount of an antibody or antibody fragment that binds a fragment set forth in SEQ ID No.: 1 of apoB100, and the antibody contains a variable heavy region ($V_H$) of SEQ ID No.: 8 and a variable light region ($V_L$) of SEQ ID No.: 9.

Methods are also provided of treating or reducing the severity of rheumatoid arthritis, accelerated atherosclerosis, or both, or treating or reducing the severity of accelerated atherosclerosis in a subject with rheumatoid arthritis, which includes administering to the subject an effective amount of an antibody or antibody fragment that binds a fragment set forth in SEQ ID No.: 1 of apoB100, and the antibody contains a heavy chain of SEQ ID No.: 10 and a light chain containing LCDR1, LCDR2 and LCDR3 as set forth in SEQ ID Nos.: 5-7, respectively. A further aspect of the embodiment provides that the method includes administering to the subject an effective amount of an antibody or antibody fragment that binds a fragment set forth in SEQ ID No.: 1 of apoB100, and the antibody contains a heavy chain of SEQ ID No.: 10 and a light chain that contains a variable light region ($V_L$) of SEQ ID No.: 9. Another aspect of the invention provides the method includes administering to the subject an effective amount of an antibody or antibody fragment that binds a fragment set forth in SEQ ID No.: 1 of apoB100, and the antibody contains a light chain of SEQ ID No.: 11 and a heavy chain that contains HCDR1, HCDR2 and HCDR3 as set forth in SEQ ID Nos.: 2-4, respectively. Yet another aspect provides the method includes administering to the subject an effective amount of an antibody or antibody fragment that binds a fragment set forth in SEQ ID No.: 1 of apoB100, and the antibody contains a light chain of SEQ ID No.: 11 and a heavy chain that contains a variable heavy region ($V_H$) of SEQ ID No.: 8. Alternatively, the method includes administering to the subject an effective amount of an antibody or antibody fragment that binds a fragment set forth in SEQ ID No.: 1 of apoB100, and the antibody contains a heavy chain of SEQ ID No.: 10 and a light chain of SEQ ID No.: 11.

Methods are also provided of reducing the likelihood of rheumatoid arthritis, accelerated atherosclerosis, or both, or providing passive immunity to a subject against rheumatoid arthritis, accelerated atherosclerosis, or both, or treating or reducing the likelihood of accelerated atherosclerosis in a subject with rheumatoid arthritis, which includes administering to the subject an effective amount of an antibody or antibody fragment that binds a fragment set forth in SEQ ID No.: 1 of apoB100, and the antibody contains a heavy chain of SEQ ID No.: 10 and a light chain containing LCDR1, LCDR2 and LCDR3 as set forth in SEQ ID Nos.: 5-7, respectively. A further aspect of the embodiment provides that the method includes administering to the subject an effective amount of an antibody or antibody fragment that binds a fragment set forth in SEQ ID No.: 1 of apoB100, and the antibody contains a heavy chain of SEQ ID No.: 10 and a light chain that contains a variable light region ($V_L$) of SEQ ID No.: 9. Another aspect of the invention provides the method includes administering to the subject an effective amount of an antibody or antibody fragment that binds a fragment set forth in SEQ ID No.: 1 of apoB100, and the antibody contains a light chain of SEQ ID No.: 11 and a heavy chain that contains HCDR1, HCDR2 and HCDR3 as set forth in SEQ ID Nos.: 2-4, respectively. Yet another aspect provides the method includes administering to the subject an effective amount of an antibody or antibody fragment that binds a fragment set forth in SEQ ID No.: 1 of apoB100, and the antibody contains a light chain of SEQ ID No.: 11 and a heavy chain that contains a variable heavy region ($V_H$) of SEQ ID No.: 8. Alternatively, the method includes administering to the subject an effective amount of an antibody or antibody fragment that binds a fragment set forth in SEQ ID No.: 1 of apoB100, and the antibody contains a heavy chain of SEQ ID No.: 10 and a light chain of SEQ ID No.: 11.

Further embodiments of the methods include administering an inhibitor of native LDL, oxidized LDL (oxLDL) or MDA-modified LDL, which are suitable for treatment of a subject diagnosed with rheumatoid arthritis, accelerated atherosclerosis, or both and reducing the severity of rheumatoid arthritis, accelerated atherosclerosis, or both, and optionally also reducing the severity or the likelihood of developing atherosclerosis, in the subject. In one embodiment, the inhibitor is an anti-oxLDL antibody or an antigen-binding fragment thereof capable of binding an oxidized fragment of apolipoprotein B100. In another embodiment, the inhibitor of oxidized LDL is a small molecule, a polypeptide, a peptide, or a nucleic acid molecule, which is capable of binding an oxidized fragment of apolipoprotein B100. In other embodiments, the inhibitor of oxidized LDL is an antibody or an antigen-binding fragment capable of binding a malondialdehyde-modified LDL. In exemplary embodiments, the inhibitor of oxidized or malondialdehyde-modified LDL is a monoclonal antibody, such as orticumab, targeting an oxidized or MDA-modified form of a LDL.

Patient Selection

The methods disclosed herein, in some embodiments, include treating or inhibiting one or more forms of rheumatoid arthritis, accelerated atherosclerosis, or both, or treating or inhibiting accelerated atherosclerosis in a subject with rheumatoid arthritis, with administering an effective amount of orticumab to a subject in need of treatment or prevention of rheumatoid arthritis, accelerated atherosclerosis, or both.

Some embodiments provided in the disclosed methods further include selecting a subject showing symptoms of rheumatoid arthritis, accelerated atherosclerosis, or both or having been diagnosed with rheumatoid arthritis, accelerated atherosclerosis, or both.

A further aspect of the invention provides the methods of treating, reducing the severity of rheumatoid arthritis, accelerated atherosclerosis, or both, and/or reducing the likelihood of rheumatoid arthritis, accelerated atherosclerosis, or both, or treating or reducing the severity or likelihood of accelerated atherosclerosis in a subject with rheumatoid arthritis, include administering to the subject an antibody or antibody fragment thereof according to any of the aforementioned antibody features, wherein the subject exhibits symptoms of rheumatoid arthritis, accelerated atherosclerosis, or both or has been diagnosed with rheumatoid arthritis, accelerated atherosclerosis, or both.

For example, subjects with rheumatoid arthritis, accelerated atherosclerosis, or both can be characterized by an elevated amount of TNFα, IL-6, CRP, MCP-1, or a combination thereof, compared to a control subject free of rheumatoid arthritis, accelerated atherosclerosis, or both. Subjects with rheumatoid arthritis can be further characterized by having joint pain, tenderness, swelling or stiffness for six weeks or longer; or morning stiffness for 30 minutes or longer.

Combination Therapy

Further embodiments provide that the methods of treating or reducing the severity of rheumatoid arthritis, accelerated atherosclerosis, or both, or treating or reducing the severity of accelerated atherosclerosis in a subject with rheumatoid arthritis, include administering an effective amount of an antibody or antibody fragment in combination with another therapeutic agent to the subject. Embodiments are also provided of the methods of reducing the likelihood of rheumatoid arthritis, accelerated atherosclerosis, or both in a subject, or treating or reducing the likelihood of accelerated atherosclerosis in a subject with rheumatoid arthritis, which includes administering an effective amount of an antibody or antibody fragment in combination with another therapeutic agent to the subject. Exemplary therapeutic agents for use in this combination include bis-phenyl (2-halophenyl)-1-imidazolylmethane or clotrimazole (disclosed in U.S. Pat. No. 4,073,922), tinidazole (U.S. Pat. No. 4,119,723), nitroimidazole, and various other anti-protozoal drugs such as 4-aminoquinolines (chloroquine), hydroxychloroquine (plaquenil), amodiaquine (camoquin), copper sulphate, bile salts (dehydrocholine), clotrimazole (canesten), suramin, pentamidine, dehydroemetine (DHE or mebadin), metronidazole (flagyl), nimorazole (naxogin (Erba)), phanquone (entobex) and diloxanide (furamide). Other suitable therapeutic agents for use in combination with an anti-oxidized LDL antibody includes anti-TNF antibodies, anti-TNF peptides and nucleic acids encoding therefor. TNF stands for tumor necrosis factor, including TNFα and TNFβ. In other aspects, the additional therapeutic agent to an anti-oxidized LDL antibody is a disease-modifying anti-rheumatic drug (DMARD), such as azathioprine, cyclophosphamide, cyclosporine, hydroxychloroquine sulfate, leflunomide, methotrexate, mycophenolate mofetil, and sulfasalazine.

The methods may also include administering an antibody or antibody fragment that binds SEQ ID No.:1, another therapeutic agent, and commonly used adjuvants to enhance absorption of the antibody or mixture of antibodies.

In various embodiments, the composition to be administered in the disclosed methods are formulated for delivery via any route of administration. For example, the methods include administration via an aerosol, nasal, oral, transmucosal, transdermal, parenteral or enteral route. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, sub arachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by injection.

Dosage

Typically, an effective amount of the anti-oxLDL or an anti-LDL antibody, or the antibody that binds SEQ ID No.:1, in the method disclosed herein, results in a plasma concentration of at least 4 μg/mL, preferably at least 12 μg/mL in the subject.

Embodiments provide the method of treating or reducing the severity of rheumatoid arthritis, accelerated atherosclerosis, or both in a subject, or treating or reducing the severity of accelerated atherosclerosis in a subject with rheumatoid arthritis, includes administering to the subject an antibody or antibody fragment disclosed above subcutaneously at about 330 mg/month for about 3, 4, 5, 6, 7, 8, 9, 10, 11 or 12 months or longer, and the subject is an adult human.

Other embodiments provide administering the antibody or antibody fragment to treat rheumatoid arthritis, accelerated atherosclerosis, or both, or treating or reducing the severity of accelerated atherosclerosis in a subject with rheumatoid arthritis, or provide passive immunity with at least 8 mg orticumab/kg of a patient (e.g., 664 mg for an averaged human patient of 83 kg). Some embodiments provide administering the antibody or antibody fragment at between 5 mg orticumab/kg of a patient (e.g., 415 mg for an averaged human patient of 83 kg) and 8 mg/kg. Some embodiment provides administering orticumab at a monthly dosing regimen at the above-mentioned dosage.

Other embodiments provide administering the antibody or antibody fragment to treat rheumatoid arthritis, or treat accelerated atherosclerosis in a subject with rheumatoid arthritis, weekly at no less than 2 mg/kg/week (166 mg for an averaged human patient of 83 kg); preferably, 4 mg/kg/week (332 mg for an averaged human patient of 83 kg). In another aspect, the composition of an anti-oxLDL antibody is administered biweekly at >2.5 mg/kg/two weeks (e.g., 208 mg for an averaged human patient of 83 kg). In yet another aspect, the composition of an anti-oxLDL antibody is administered monthly at about 6 mg/kg/month (e.g., about 498 mg for an averaged human patient of 83 kg). For example, the monthly dosing may be carried out for 12 months or 3 months.

Yet other embodiments provide administering an antibody or antibody fragment to treat rheumatoid arthritis, or treat accelerated atherosclerosis in a subject with rheumatoid arthritis, with at least an initial dose of 800-900 mg, 900-1000 mg, 1000-1100 mg, 1100-1200 mg, 1200-1300 mg, 1300-1400 mg, 1400-1500 mg, or 1500-1600 mg. In some aspects, the effective amount in the method described herein includes an initial dose of orticumab of approximately 1000-1500 mg, followed by subsequent doses of the antibody at 700-900 mg administered weekly for 2, 3, 4 or 5 weeks and/or even administered monthly for 1, 2 or 3 months.

Other embodiments provide administering step-wise escalating doses of an antibody against native or oxidized LDL (e.g., binding SEQ ID No.:1). In this embodiment, an exemplary (starting) dose of a single-dose administration of an antibody (e.g., orticumab) against native or oxidized LDL is between 0.005 and 0.01 mg/kg (e.g., intravenously); and other exemplary dosage levels to be administered in the single-dose administration are between 0.01 and 0.15, between 0.15 and 0.75, between 0.75 and 2.5, between 2.5 and 7.5, and between 7.5 and 30 mg/kg (e.g., intravenously). For example, a starting dose of orticumab in a single-dose intravenous administration is 0.007 mg/kg; and other exemplary dosages can be 0.05, 0.25, 1.25, 5.0 or 15.0 mg/kg in subsequent single-dose intravenous administration. In another embodiment, a single-dose subcutaneous administration of an antibody against native or oxidized LDL is between 0.5 and 5 mg/kg, and a multiple-dose subcutaneous administration is also between 0.5 and 5 mg/kg. For example, an antibody against native or oxidized LDL at 1.25 mg/kg is administered subcutaneously. In various embodiments, the dosage is administered within a specified hour range of the day in each administration, and each dose in a multiple-dose treatment (e.g., 4 doses, 3 doses, 5 doses, or 6 doses) is administered at weekly intervals with a time window of ±1 day. In another example, an antibody (such as orticumab) against native or oxidized LDL is administered at between 300 mg and 450 mg (e.g., 360 mg) to a human subject, optionally followed by another dose between 300 mg and 450 mg (e.g., 360 mg) to the human subject where the second dose is at least 70 days (up to 91 days) apart from the first dose. The antibody (such as orticumab) may be formulated at a concentration of 100-170 mg/mL (e.g., 150 mg/mL) and for use in subcutaneous administration without further dilution, or diluted to a large volume for intravenous infusion.

Further embodiments include administering to a subject an effective amount of an antibody or antibody fragment that binds SEQ ID No.:1 and having a sequence of one or more of SEQ ID Nos: 2-11, which is in the range of about 10-50 μg/period, 50-100 μg/period, 100-150 μg/period, 150-200 μg/period, 100-200 μg/period, 200-300 μg/period, 300-400 μg/period, 400-500 μg/period, 500-600 μg/period, 600-700 μg/period, 700-800 μg/period, 800-900 μg/period, 900-1000 μg/period, 1000-1100 μg/period, 1100-1200 μg/period, 1200-1300 μg/period, 1300-1400 μg/period, 1400-1500 μg/period, 1500-1600 μg/period, 1600-1700 μg/period, 1700-1800 μg/period, 1800-1900 μg/period, 1900-2000 μg/period, 2000-2100 μg/period, 2100-2200 μg/period, 2200-2300 μg/period, 2300-2400 μg/period, 2400-2500 μg/period, 2500-2600 μg/period, 2600-2700 μg/period, 2700-2800 μg/period, 2800-2900 μg/period or 2900-3000 μg/period. A period is a day, a week, a month, or another length of time. One aspect is the antibody (e.g., orticumab) is administered at a weekly, biweekly or monthly frequency of any of above-mentioned dosage per period.

In some embodiments, the methods include administering an inhibitor of oxidized LDL (e.g., orticumab) to the subject for 1-5 days, 1-5 weeks, 1-5 months, or 1-5 years. For example, the antibody is administered to the subject in 3, 4, 5, 6, 7, 8, 9, 10, 11, 12, 13, 14, 15, 16, 17, 18, 19 or 20 doses, each dose separated by at least 3 days, 5 days, one week, two weeks, one month, two months, or a combination thereof. In other embodiments, the second dose is administered about 2-3 weeks, or about 3 weeks after the first dose and the third dose is administered about 5-6 weeks or about 6 weeks after the first dose, etc. In another embodiment, the second dose is administered about 2-3 months, about 2 months, about 3 months or about 4 months after the first dose and the third dose is administered about 4-6 months, about 5-6 months, about 5 months or about 6 months after the first dose.

Other embodiments provide administering step-wise escalating doses of an antibody against native or oxidized LDL to treat rheumatoid arthritis, or treat accelerated atherosclerosis in a subject with rheumatoid arthritis, or provide passive immunity. In this embodiment, an exemplary (starting) dose of a single-dose administration of an antibody (e.g., orticumab) against native or oxidized LDL is between 0.005 and 0.01 mg/kg (e.g., intravenously); and other exemplary dosage levels to be administered in the single-dose administration are between 0.01 and 0.15, between 0.15 and 0.75, between 0.75 and 2.5, between 2.5 and 7.5, and between 7.5 and 30 mg/kg (e.g., intravenously). For example, a starting dose of orticumab in a single-dose intravenous administration is 0.007 mg/kg; and other exemplary dosages can be 0.05, 0.25, 1.25, 5.0 or 15.0 mg/kg in subsequent single-dose intravenous administration. In another embodiment, a single-dose subcutaneous administration of an antibody against native or oxidized LDL is between 0.5 and 5 mg/kg, and a multiple-dose subcutaneous administration is also between 0.5 and 5 mg/kg. For example, an antibody against native or oxidized LDL at 1.25 mg/kg is administered subcutaneously. In various embodiments, the dosage is administered within a specified hour range of the day in each administration, and each dose in a multiple-dose treatment (e.g., 4 doses, 3 doses, 5 doses, or 6 doses) is administered at weekly intervals with a time window of ±1 day. In another example, an antibody (such as orticumab) against native or oxidized LDL is administered at between 300 mg and 450 mg (e.g., 360 mg) to a human subject, optionally followed by another dose between 300 mg and 450 mg (e.g., 360 mg) to the human subject where the second dose is at least 70 days (up to 91 days) apart from the first dose. The antibody (such as orticumab) may be formulated at a concentration of 100-170 mg/mL (e.g., 150 mg/mL) and for use in subcutaneous administration without further dilution, or diluted to a large volume for intravenous infusion. In some embodiments, the therapeutically effective amount of an anti-LDL antibody or an anti-oxLDL antibody, or analogs, pharmaceutical equivalents or a peptidomimetics thereof, for use with the methods described herein is per dose: 1-10 µg/kg, 10-100 µg/kg, 100-500 µg/kg, 200-500 µg/kg, 300-500 µg/kg, 400-500 µg/kg, 1-5 mg/kg, 5-10 mg/kg, 10-15 mg/kg, 15-20 mg/kg, 20-25 mg/kg, 25-50 mg/kg, 50-75 mg/kg of the subject; where each dose is administered daily, weekly, monthly, or at other intervals.

In some embodiments, an instruction manual for use, a vial for diluent, or both are also included in the kit, in addition to the one or the plurality of vials/doses of the antibody or antibody fragment to treat rheumatoid arthritis, accelerated atherosclerosis, or both.

Compositions or Medicaments

In various embodiments, the present invention provides a pharmaceutical composition for use in the methods of treating, reducing the severity of rheumatoid arthritis, accelerated atherosclerosis, or both and/or reducing the likelihood of rheumatoid arthritis, accelerated atherosclerosis, or both described herein. The pharmaceutical composition includes an inhibitor of oxidized LDL, such as an anti-oxLDL antibody that binds to an epitope of SEQ ID No.:1 of ApoB100, and a pharmaceutically acceptable carrier. Further embodiments provide that a composition or medicament for use in treating, reducing the severity of, or promoting prophylaxis against rheumatoid arthritis, or treating, reducing the severity of, or promoting prophylaxis against atherosclerosis in a subject exhibiting symptoms of or having been diagnosed with rheumatoid arthritis, where the composition of medicament contains an anti-oxLDL antibody that binds to an epitope of SEQ ID No.:1 of ApoB100, as disclosed above, in an amount of between 300 mg and 400 mg, preferably about 330 mg, per dosage (or vial), optionally with a pharmaceutically acceptable carrier, each (e.g., for a monthly subcutaneous administration to a subject) for 1, 2, 3, 4, 5, 6, 7, 8, 9, 10, 11, 12 months or longer. Other embodiments provide the composition or medicament contains an anti-oxLDL antibody that binds to an epitope of SEQ ID No.:1 of ApoB100, as disclosed above, in an amount of at least 5, 6, 7, or 8 mg orticumab/kg of a patient in one dosage (or vial), and optionally more dosages (or vials) of at least 2 mg/kg/week, at least 2.5 mg/kg/two weeks, or at least 6 mg/kg/month, for 3, 4, 5, 6, 7, 8, 9, 10, 11, 12 months or longer. Further embodiments provide the composition or medicament contains the antibody (such as orticumab) at a concentration of 100-170 mg/mL (e.g., 150 mg/mL) and for use in subcutaneous administration without further dilution, or diluted to a large volume for intravenous infusion.

"Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof. Generally, each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Prepare Antibodies in the Methods

In some embodiments, the aforementioned methods involve antibodies that bind to a specific antigen epitope, where the antibodies contain one or more defined sequences. For example, modern recombinant library technology is used to prepare therapeutic antibodies against native ApoB, oxidized ApoB or MBA-modified ApoB. While murine hybridomas cells produce large amounts of identical antibodies, these non-human antibodies are recognized by human body as foreign, and as a consequence, their efficacy and plasma half-lives are decreased in addition to eliciting allergic reactions. To solve this problem, one approach is to make chimeric antibodies where the murine variable domains of the antibody are transferred to human constant regions resulting in an antibody that is mainly human. A further refinement of this approach is to develop humanized antibodies where the regions of the murine antibody that contacted the antigen, the so called Complementarity Determining Regions (CDRs) are transferred to a human antibody framework, resulting in a humanized antibody. Another approach is to produce completely human antibodies using recombinant technologies, which does not rely on immunization of animals to generate the specific antibody. Instead recombinant libraries comprise a huge number of pre-made antibody variants and it is likely that a library will have at least one antibody specific for any antigen. A phage display system may be used where antibody fragments are expressed, displayed, as fusions with phage coat proteins on the surface of filamentous phage particles, while the phage display system simultaneously carries the genetic information encoding the displayed molecule. Phage displaying antibody fragments specific for a particular antigen may be selected through binding to the antigen in question. Isolated phage may then be amplified and the gene encoding the selected antibody variable domains may optionally be transferred to other antibody formats as e.g. full length immunoglobulin and expressed in high amounts using appropriate vectors and host cells well known in the art. The format of displayed antibody specificities on phage particles may differ. The most commonly used formats are Fab and single chain (scFv) both containing the variable antigen binding domains of antibodies. The single chain format is composed of a variable heavy domain ($V_H$) linked to a variable light domain ($V_L$) via a flexible linker. Before use as analytical reagents, or therapeutic agents, the displayed antibody specificity is transferred to a soluble format, e.g., Fab or scFv, and analyzed as such. In later steps the antibody fragment identified to have desirable characteristics may be transferred into yet other formats such as full length antibodies.

Antibody Production Using Hybridomas

The cell fusions are accomplished by standard procedures well known to those skilled in the field of immunology. Fusion partner cell lines and methods for fusing and selecting hybridomas and screening for mAbs are well known in the art. See, e.g., Ausubel infra, Harlow infra, and Colligan infra, the contents of which references are incorporated entirely herein by reference.

An anti-oxidized LDL antibody can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a non-murine hybridoma (e.g., rat or human), hybridoma cells are preferably grown in irradiated or athymic nude mice. Alternatively, the antibodies can be produced by culturing hybridoma or transfectoma cells in vitro and isolating secreted mAb from the cell culture medium or recombinantly, in eukaryotic or prokaryotic cells.

Recombinant Expression of Anti-Oxidized LDL Antibodies

Recombinant murine or chimeric murine-human or human-human antibodies that inhibit oxidized LDL can be provided according to the present invention using known techniques based on the teaching provided herein. See, e.g., Ausubel et al., eds. Current Protocols in Molecular Biology, Wiley Interscience, N.Y. (1987, 1992, 1993); and Sambrook et al. Molecular Cloning: A Laboratory Manual, Cold Spring Harbor Laboratory Press (1989).

The DNA encoding an anti-oxidized LDL antibody can be genomic DNA or cDNA which encodes at least one of the heavy chain constant region (Hc), the heavy chain variable region (Hc), the light chain variable region (Lv) and the light chain constant regions (Lc). A convenient alternative to the use of chromosomal gene fragments as the source of DNA encoding the murine V region antigen-binding segment is the use of cDNA for the construction of chimeric immunoglobulin genes, e.g., as reported by Liu et al. (Proc. Natl. Acad. Sci., USA 84:3439 (1987) and J. Immunology 139: 3521 (1987). The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1. Anti-oxLDL Inhibits Inflammatory In Vitro and In Vivo

Figure 1A:
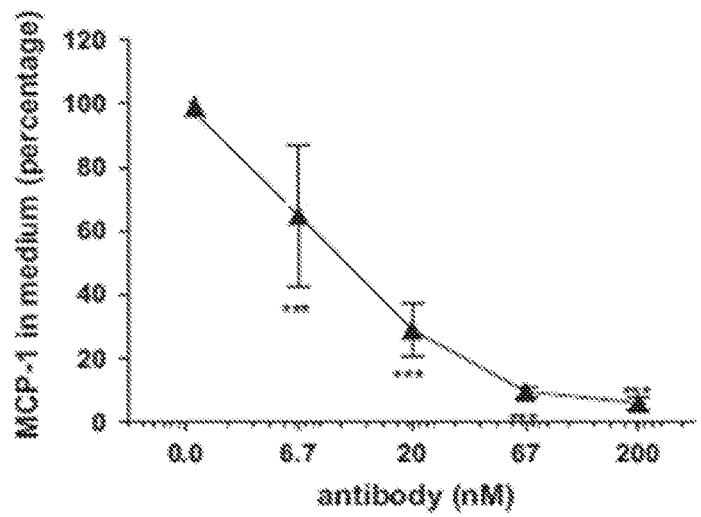
FIGS. 1A and 1B depict that anti-oxLDL monoclonal antibody inhibits inflammation in vitro.
Figure 1B:
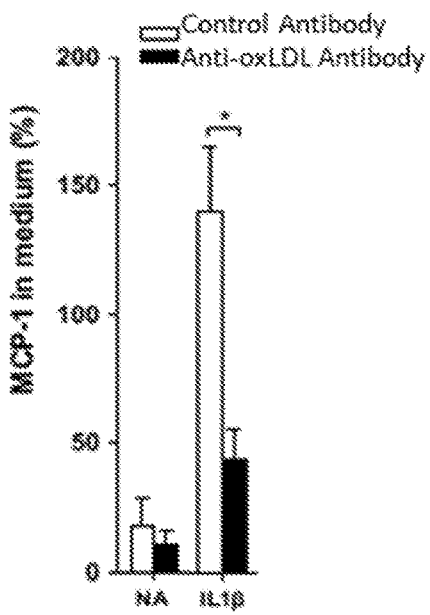

Plates were coated with 3 µg/mL oxLDL to stimulate primary monocytes. Anti-oxLDL antibody (orticumab) was added at increasing concentrations, and relative MCP-1 protein in cell culture supernatant was measured; MCP-1 levels from cells without antibody treatment was set to 100%. We found that an anti-oxLDL antibody reduced inflammatory activity of primary monocytes, the precursors to macrophage cells. This antibody reduced the secretion of the pro-inflammatory mediator monocyte chemoattractant protein 1 (MCP-1), and this reduction occurred under conditions in which primary monocytes were stimulated with oxLDL, as well as IL-1β (FIGS. 1A and 1B). A study in adult non-human primates fed with a high-fat, high-fructose diet (HFFD) showed that the levels of TNFα and IL-1β in plasma were both reduced in response to treatment with the anti-oxLDL antibody (FIGS. 2A and 2B). Changes in plasma inflammatory cytokines in response to diet and to the anti-oxLDL antibody treatment (weekly intravenous administration at 10 mg/kg over 12 weeks for a total of 13 doses) in rhesus macaques (n=6) were measured. FIG. 2A shows TNFα was significantly increased in animals fed with a high-fat, high-fructose diet (HFFD) (two-tailed t-test; p<0.0001) compared to control animals when measured by ELISA. Treatment with an anti-oxLDL antibody significantly reduced the level of TNFα, compared to that in week 0, from week 8 to at least week 24 (repeated measures ANOVA with Dunnett's posthoc analysis). FIG. 2B shows HFFD significantly increased IL-1β levels (two-tailed t-test; p<0.001) and the anti-oxLDL antibody treatment significantly improved IL-1β levels (i.e., reduced the amount of IL-1β) starting from 4 weeks after treatment was initiated and onward. The level of IL-1β was still significantly lower 24 weeks after the start of treatment.

Together, the data demonstrated that exogenous administration of an anti-oxLDL antibody reduces the pro-inflammatory environment that contributes to RA and its associated complications, specifically accelerated atherosclerosis.

Example 2. Pharmacokinetics (PK) of Anti-oxLDL Antibody

The ability of orticumab to shut down macrophage pro-inflammatory activity locally in the plaque became the focus, as it was thought to be an important mechanism underlying its therapeutic activity. Initial hypothesis of using orticumab related to neutralizing oxLDL from the systemic compartment, which required 4 μg/mL=~28 nM=11 mg of orticumab to neutralize 90% systemic oxLDL. Further in vitro assays provided an insight into the minimum effective concentration of orticumab needed to achieve 50% or 90% inhibition of oxLDL-mediated cytokine release (i.e., inhibition of monocyte chemoattractant protein 1, MCP-1):

$IC_{50}$ for MCP-1 inhibition: ~10 nM=1.5 μg/mL=~4 mg
$IC_{90}$ for MCP-1 inhibition: ~30-80 nM=4.5–12 μg/mL=12.4-33 mg.

A dosage regimen containing an initial dose of 1245 mg, followed by subsequent 830 mg weekly×3, then 830 mg monthly×2, compared to the range of $IC_{90}$ for MCP-1 inhibition (i.e., 12.4 mg orticumab), was 100 times (initially) and 67 times (subsequently) greater than the 12.4 mg (lower end of $IC_{90}$ for MCP-1 inhibition). The dosage regimen containing an initial dose of 1245 mg, followed by 830 mg weekly×3, then 830 mg monthly×2, compared to the higher range (33 mg orticumab) as $IC_{90}$ for MCP-1 inhibition, was 38 times (initially) and 25 times (subsequently) greater than the 33 mg (higher end of $IC_{90}$ for MCP-1 inhibition).

In patients with atherosclerosis, it has been reported that there is an increased endothelial permeability to macromolecules, where uptake of injected macromolecules into the arterial wall is rapid and linear over time and the equilibrium against circulating blood stream is reached within 1 hour.

Based on this background information, we proposed a loading dosage that would yield steady state plasma concentration of orticumab of at least 12 μg/mL for up to 96 hours in a simulation model (FIG. 3). The loading dose of 8 mg/kg (664 mg for an averaged patient of 83 kg), followed by bi-weekly to weekly 2 mg/kg (166 mg) subcutaneous (SC) dosing. This loading dose was 1.9 times less than the loading dose, and the weekly dosing was 5 times less than the weekly dosing than a dosage regimen containing an initial dose of 1245 mg, followed by subsequent 830 mg weekly×3, then 830 mg monthly×2.

In another set of simulations based on SC dosing:

(1) Weekly dosing at 2 mg/kg (166 mg) achieved 12 μg/mL threshold between Day 2-4 (FIG. 4A);

(2) Biweekly dosing at 2 mg/kg did not achieve 12 μg/mL threshold, but did achieve 4 μg/mL threshold from Day 1-6 (FIG. 4A);

(3) Monthly dosing at 2 mg/kg did not achieve sustained exposure at the 4 μg/mL threshold (FIG. 4A);

(4) Loading Dose of 5 mg/kg (415 mg), followed by biweekly dosing at 2 mg/kg did not achieve 12 μg/mL threshold, but did maintain exposure above the 4 μg/mL through Day 6 (FIG. 4B).

In clinical trials of orticumab, Tables 1-4 below summarize the PK data.

TABLE 1

The PK data from a "FIH" trial with single dosing.

| Dose (mg/kg) | Route of Admin | $C_{max}$ (μg/mL) | C ≥ 1 μg/mL | C ≥ 4 μg/mL | C ≥ 12 μg/mL |
|---|---|---|---|---|---|
| 1.25 | SC | 2.99 | Day 28 | Not achieved | Not achieved |
| 1.25 | IV | 20.6 | Day 28 | Day 3 (<Day 7) | 11 hours |
| 5 | IV | 105 | Day 56 | Day 14 | Day 3 |
| 15 | IV | 286 | Day 70* | Day 42 | Day 28 |

*Last day of assessment

TABLE 2

The PK data from a "FIH" trial with multiple dosing.

| Dose (mg/kg) | Route of Admin | $C_{max}$ (μg/mL) | C ≥ 1 μg/mL | C ≥ 4 μg/mL | C ≥ 12 μg/mL |
|---|---|---|---|---|---|
| 1.25 | SC | 1.24 | Day 42 | Not achieved | Not achieved |
| 1.25 | IV | 29.6 | Day 70 | Day 28 | Day 23 |
| 5 | IV | 105 | Day 91* | Day 56 | Day 35 |
| 15 | IV | 303 | Day 91* | Day 91 | Day 56 |

*Last day of assessment

TABLE 3

The PK data from a "Ph1" trial with single dosing comparing subcutaneous (SC) and intravenous (IV) administration.

| Dose (mg/kg) | Route of Admin | $C_{max}$ (μg/mL) | C ≥ 1 μg/mL | C ≥ 4 μg/mL | C ≥ 12 μg/mL |
|---|---|---|---|---|---|
| 360 | SC | 9.15 | Day 43 | Day 15 | Not achieved |
| 360 | SC 70-90 days after IV dosing | 15.1 | Day 57 | Day 15 | Day 8 |
| 360 | IV | 84.3 | Day 57* | Day 15 | Day 8 |

*Last day of assessment

TABLE 4

| | | The PK data from a "Ph2" trial. | | | | |
|---|---|---|---|---|---|---|
| Dose Group | Route of Admin | $C_{max}$ (μg/mL) D1 | D78* | C ≥ 1 μg/mL | C ≥ 4 μg/mL | C ≥ 12 μg/mL |
| Single Dose | IV | 297 | N/A | Day 106 | Day 50 | Day 22 |
| Multiple Dose | IV | 286 | 197 | Day 169 | Day 141 | Day 106 |

Dosing days: D1, 8, 15, 22, 50, 78
*Last day of dosing

Cmax, Single Dose at 1.25 mg/kg: 1.25 mg/kg=104 mg, which was 6.9 times greater max exposure with IV vs SC admin (½-life is 20 days for both); SC dose does not reach threshold of 4-12 μg/mL.

Cmax, Single Dose at 360 mg: 360 mg=4.34 mg/kg (3.5 times FIH study), 9.2 times greater max exposure with IV vs SC admin (½-life is 33.5 vs 24.3 days, IV vs SC); SC dose falls within range of 4-12 μg/mL.

As a result, based on the simulated and actual PK data, 8 mg/kg (664 mg) is optimal, but 5 mg/kg (415 mg) is likely sufficient. Based on the ½-life of a single dose in the clinical studies (i.e., 24 days with a single SC dose of 360 mg), monthly dosing is reasonable.

In another set of studies of orticumab:
(1) Weekly SC dose of 1 mg/kg and above maintained concentrations above 4 μg/mL at steady state. FIG. 5 depicts the simulated human PK profiles after weekly SC dosing, using PK parameters from Phase I data. Bioavailability after SC dose is 70%.
(2) Bi-weekly SC dose of 1.5 mg/kg and above maintained concentrations above 4 μg/mL at steady state. FIG. 6 depicts the simulated human PK profiles after bi-weekly SC dosing, using PK parameters from Phase I data.
(3) Monthly SC dose of ~3 to 4 mg/kg and above maintained concentrations above 4 μg/mL. FIG. 7 depicts the simulated human PK profiles after monthly SC dosing, using parameters from Phase I data.

Based on simulated PK data, and targeting a plasma concentration of 12 μg/mL threshold for maximum chance of success, weekly dosing should be no less than 2 mg/kg (166 mg); 4 mg/kg (332) would be preferable; biweekly dosing must be >2.5 mg/kg (208 mg); higher doses were not simulated; and monthly dosing should be 6 mg/kg (498 mg). In some embodiments, final recommendation is 500 mg, monthly via SC injection. Monthly dosing of 500 mg each month can be administered 12 doses over a 12-month dosing regimen, or 3 doses over a 3-month dosing regimen. Monthly dosing of 330 mg each month (to meet the minimum 4 μg/mL plasma concentration threshold) can be administered 12 doses over a 12-month dosing regimen, or 3 doses over a 3-month dosing regimen.

In patients with CVD, patient oxLDL estimated to be 4.4 nM (0.92 mg/dL); oxLDL range in CHD: 3.1-201.3 mg/dL (Normals: 1.3-112.4 mg/dL); oxLDL range in AMI: 1.95 ng/5 μg (Normals: 0.58/5 μg). In RA patient, oxLDL range in RA patients: 0.04 mg/dL. There is a wide range of oxLDL levels among patients with CVD. There is yet no clear understanding of the amount of oxLDL in lesions (whether atherosclerosis or RA), in comparison to that in circulation. Therefore the dosing estimate for orticumab based on simulations and calculations for inhibiting MCP-1 provides feasible dosage regimens.

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

What is claimed is:

1. A method for treating, reducing the severity of, slowing progression of, or inhibiting rheumatoid arthritis in a subject in need thereof, comprising: administering to the subject an effective amount of an antibody or antibody fragment an HCDR 1 (HCDR1) having the sequence of SEQ ID NO: 2, an HCDR 2 (HCDR2) having the sequence of SEQ ID NO: 3, and an HCDR 3 (HCDR3) having the sequence of SEQ ID NO: 4, and an LCDR 1 (LCDR1) having a sequence of SEQ ID NO: 5, an LCDR 2 (LCDR2) having a sequence of SEQ ID NO: 6, and an LCDR 3 (LCDR3) having a sequence of SEQ ID NO: 7.

2. The method of claim 1, wherein the antibody comprises the variable heavy region (VH) of SEQ ID No.: 8, the variable light region (VL) of SEQ ID No.: 9, or both.

3. The method of claim 2, wherein the antibody comprises the heavy chain of SEQ ID No.: 10, the light chain of SEQ ID No.: 11, or both.

4. The method of claim 1, wherein the antibody is orticumab.

5. The method of claim 4, wherein the antibody or antibody fragment is administered in one, two or more doses of at least 5 mg/kg each or at least 8 mg/kg each.

6. The method of claim 5, further comprising administering a plurality of subsequent doses of the antibody or antibody fragment in an amount of at least 2 mg/kg/week, at least 2.5 mg/kg/two weeks, or at least 6 mg/kg/month.

7. The method of claim 5, wherein two or more doses are administered, and wherein the two or more doses are administered over at least 8 weeks, 10 weeks, or 12 weeks.

8. The method of claim 4, wherein the antibody is administered at 1-10 µg/kg, 10-100 µg/kg, 100-500 µg/kg, 200-500 µg/kg, 300-500 µg/kg, 400-500 µg/kg, 1-5 mg/kg, 5-10 mg/kg, 10-15 mg/kg, 15-20 mg/kg, 20-25 mg/kg, 25-50 mg/kg, or 50-75 mg/kg.

9. The method of claim 1, further comprising administering a therapeutic agent selected from the group consisting of azathioprine, cyclophosphamide, cyclosporine, hydroxychloroquine sulfate, leflunomide, methotrexate, mycophenolate mofetil, sulfasalazine, bis-phenyl (2-halophenyl)-1-imidazolylmethane, clotrimazole, tinidazole, nitroimidazole, 4-aminoquinolines, hydroxychloroquine, amodiaquine, copper sulphate, dehydrocholine, clotrimazole, suramin, pentamidine, dehydroemetine, metronidazole, nimorazole, phanquone, diloxanide, an anti-tumor necrosis factor (TNF) antibody, an anti-TNF peptide, and a nucleic acid encoding an anti-TNF antibody or peptide.

10. The method of claim 1, further comprising selecting a subject showing a symptom of or having been diagnosed with rheumatoid arthritis, prior to administering the effective amount of the antibody or antibody fragment thereto.

11. The method of claim 1, wherein the subject has an elevated amount of one or more pro-inflammatory cytokines in circulation selected from the group of tumor necrosis factor-alpha (TNFα), interleukin 1 beta (IL-1β), interleukin 6 (IL-6), monocyte chemoattractant protein 1 (MCP-1), and C-reactive protein (CRP), compared to a control subject free of rheumatoid arthritis.

12. The method of claim 1 for treating, reducing the severity of, slowing progression of, or inhibiting rheumatoid arthritis.

13. The method of claim 1 for treating, reducing the severity of, slowing progression of, or inhibiting accelerated atherosclerosis in a subject with symptoms of rheumatoid arthritis or having been diagnosed with rheumatoid arthritis.

14. The method of claim 1 for treating, reducing the severity of, slowing progression of, or inhibiting a combination of rheumatoid arthritis and accelerated atherosclerosis.

15. A method of reducing the severity of or the likelihood of developing inflammation in a subject, comprising: administering to the subject an effective amount of an antibody or antibody fragment wherein the antibody comprises an HCDR 1 (HCDR1) having the sequence of SEQ ID NO: 2, an HCDR 2 (HCDR2) having the sequence of SEQ ID NO: 3, and an HCDR 3 (HCDR3) Having the sequence of SEQ ID NO: 4, and an LCDR 1 (LCDR1) having a sequence of SEQ ID NO: 5, an LCDR 2 (LCDR2) having a sequence of SEQ ID NO: 6, and an LCDR 3 (LCDR3) having a sequence of SEQ ID NO: 7, wherein the subject shows symptoms of rheumatoid arthritis or has been diagnosed with rheumatoid arthritis.

16. The method of claim 15, wherein one or more markers of inflammation have a reduced level after the administration, the markers being selected from the group consisting of tumor necrosis factor-alpha (TNFα), interleukin I beta (IL-1β), interleukin 6 (IL-6), monocyte chemoattractant protein-1 (MCP-1), and C-reactive protein (CRP).

17. The method of claim 15, wherein the subject shows symptoms of accelerated atherosclerosis or has been diagnosed with accelerated atherosclerosis.

18. The method of claim 15, wherein the antibody comprises orticumab.

* * * * *

UNITED STATES PATENT AND TRADEMARK OFFICE
CERTIFICATE OF CORRECTION

| | |
|---|---|
| PATENT NO. | : 11,690,912 B2 |
| APPLICATION NO. | : 17/058508 |
| DATED | : July 4, 2023 |
| INVENTOR(S) | : Bertrand C. Liang et al. |

It is certified that error appears in the above-identified patent and that said Letters Patent is hereby corrected as shown below:

In the Claims

Column 37, Claim 1, Lines 62-63, replace "fragment an" with --fragment wherein the antibody comprises an--.

Signed and Sealed this
Seventh Day of November, 2023

*Katherine Kelly Vidal*

Katherine Kelly Vidal
*Director of the United States Patent and Trademark Office*

SEQUENCE LISTING

<160> NUMBER OF SEQ ID NOS: 11

<210> SEQ ID NO 1
<211> LENGTH: 20
<212> TYPE: PRT
<213> ORGANISM: Artificial Sequence
<220> FEATURE:
<223> OTHER INFORMATION: P45 of apoB100

```
<400> SEQUENCE: 1

Ile Glu Ile Gly Leu Glu Gly Lys Gly Phe Glu Pro Thr Leu Glu Ala
1               5                   10                  15

Leu Phe Gly Lys
            20

<210> SEQ ID NO 2
<211> LENGTH: 14
<212> TYPE: PRT
<213> ORGANISM: Artificial Sequence
<220> FEATURE:
<223> OTHER INFORMATION: HCDR1

<400> SEQUENCE: 2

Phe Ser Asn Ala Trp Met Ser Trp Val Arg Gln Ala Pro Gly
1               5                   10

<210> SEQ ID NO 3
<211> LENGTH: 19
<212> TYPE: PRT
<213> ORGANISM: Artificial Sequence
<220> FEATURE:
<223> OTHER INFORMATION: HCDR2

<400> SEQUENCE: 3

Ser Ser Ile Ser Val Gly Gly His Arg Thr Tyr Tyr Ala Asp Ser Val
1               5                   10                  15

Lys Gly Arg

<210> SEQ ID NO 4
<211> LENGTH: 14
<212> TYPE: PRT
<213> ORGANISM: Artificial Sequence
<220> FEATURE:
<223> OTHER INFORMATION: HCDR3

<400> SEQUENCE: 4

Ala Arg Ile Arg Val Gly Pro Ser Gly Gly Ala Phe Asp Tyr
1               5                   10

<210> SEQ ID NO 5
<211> LENGTH: 14
<212> TYPE: PRT
<213> ORGANISM: Artificial Sequence
<220> FEATURE:
<223> OTHER INFORMATION: LCDR1

<400> SEQUENCE: 5

Cys Ser Gly Ser Asn Thr Asn Ile Gly Lys Asn Tyr Val Ser
1               5                   10

<210> SEQ ID NO 6
<211> LENGTH: 7
<212> TYPE: PRT
<213> ORGANISM: Artificial Sequence
<220> FEATURE:
<223> OTHER INFORMATION: LCDR2

<400> SEQUENCE: 6

Ala Asn Ser Asn Arg Pro Ser
1               5

<210> SEQ ID NO 7
<211> LENGTH: 12
<212> TYPE: PRT
```

<213> ORGANISM: Artificial Sequence
<220> FEATURE:
<223> OTHER INFORMATION: LCDR3

<400> SEQUENCE: 7

Cys Ala Ser Trp Asp Ala Ser Leu Asn Gly Trp Val
1               5                   10

<210> SEQ ID NO 8
<211> LENGTH: 120
<212> TYPE: PRT
<213> ORGANISM: Artificial Sequence
<220> FEATURE:
<223> OTHER INFORMATION: Variable heavy region

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Ser Ile Ser Val Gly Gly His Arg Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Arg Val Gly Pro Ser Gly Gly Ala Phe Asp Tyr Trp Gly
            100                 105                 110

Gln Gly Thr Leu Val Thr Val Ser
        115                 120

<210> SEQ ID NO 9
<211> LENGTH: 110
<212> TYPE: PRT
<213> ORGANISM: Artificial Sequence
<220> FEATURE:
<223> OTHER INFORMATION: Variable light region

<400> SEQUENCE: 9

Gln Ser Val Leu Thr Gln Pro Pro Ser Ala Ser Gly Thr Pro Gly Gln
1               5                   10                  15

Arg Val Thr Ile Ser Cys Ser Gly Ser Asn Thr Asn Ile Gly Lys Asn
            20                  25                  30

Tyr Val Ser Trp Tyr Gln Gln Leu Pro Gly Thr Ala Pro Lys Leu Leu
        35                  40                  45

Ile Tyr Ala Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Ala Ser Leu
                85                  90                  95

Asn Gly Trp Val Phe Gly Gly Gly Thr Lys Leu Thr Val Leu
            100                 105                 110

<210> SEQ ID NO 10
<211> LENGTH: 451
<212> TYPE: PRT
<213> ORGANISM: Artificial Sequence
<220> FEATURE:
<223> OTHER INFORMATION: Heavy chain

<400> SEQUENCE: 10

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Ser Ser Ile Ser Val Gly Gly His Arg Thr Tyr Tyr Ala Asp Ser Val
     50                  55                  60

Lys Gly Arg Ser Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile Arg Val Gly Pro Ser Gly Gly Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 11
<211> LENGTH: 216
<212> TYPE: PRT
<213> ORGANISM: Artificial Sequence
<220> FEATURE:
<223> OTHER INFORMATION: Light chain

<400> SEQUENCE: 11

Gln Ser Val Leu Thr Gln Pro Pro Ser Ala Ser Gly Thr Pro Gly Gln
1               5                   10                  15

Arg Val Thr Ile Ser Cys Ser Gly Ser Asn Thr Asn Ile Gly Lys Asn
            20                  25                  30

Tyr Val Ser Trp Tyr Gln Gln Leu Pro Gly Thr Ala Pro Lys Leu Leu
            35                  40                  45

Ile Tyr Ala Asn Ser Asn Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Ala Ser Leu
            85                  90                  95

Asn Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215
```